United States Patent
Aoyama et al.

(10) Patent No.: US 9,530,571 B2
(45) Date of Patent: Dec. 27, 2016

(54) COMPOUND AND SUPPORT MATERIAL SUPPORTING THIS NOVEL COMPOUND

(75) Inventors: Yohei Aoyama, Tokyo (JP); Kazuyuki Noda, Tokyo (JP); Hiroyuki Osada, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 243 days.

(21) Appl. No.: 14/350,171

(22) PCT Filed: Aug. 21, 2012

(86) PCT No.: PCT/JP2012/071093
§ 371 (c)(1),
(2), (4) Date: Apr. 7, 2014

(87) PCT Pub. No.: WO2013/073243
PCT Pub. Date: May 23, 2013

(65) Prior Publication Data
US 2014/0261647 A1    Sep. 18, 2014

(30) Foreign Application Priority Data
Nov. 18, 2011 (JP) ................................. 2011-253132

(51) Int. Cl.
| | |
|---|---|
| C07F 7/10 | (2006.01) |
| H01G 9/20 | (2006.01) |
| C09B 69/00 | (2006.01) |
| C07F 15/00 | (2006.01) |
| C07F 7/18 | (2006.01) |
| H01L 51/00 | (2006.01) |

(52) U.S. Cl.
CPC ........... H01G 9/2059 (2013.01); C07F 7/1856 (2013.01); C07F 15/0053 (2013.01); C09B 69/008 (2013.01); H01L 51/006 (2013.01); H01L 51/0061 (2013.01); H01L 51/0094 (2013.01); *H01G 9/204* (2013.01); *H01G 9/2031* (2013.01); *H01L 51/0068* (2013.01); *H01L 51/0069* (2013.01); *H01L 51/0072* (2013.01); *H01L 51/0086* (2013.01); *Y02E 10/542* (2013.01)

(58) Field of Classification Search
CPC .................................................... H01G 9/2059
USPC ........................................................ 556/419
See application file for complete search history.

(56) References Cited

U.S. PATENT DOCUMENTS

| | | | |
|---|---|---|---|
| 4,460,739 A | 7/1984 | Ashby | |
| 5,627,227 A * | 5/1997 | Suga ................... | C07F 7/0854 524/91 |
| 6,521,769 B1 | 2/2003 | Zhang | |
| 7,687,635 B2 | 3/2010 | Verpoort et al. | |
| 7,976,585 B2 | 7/2011 | Cremer et al. | |
| 2002/0115753 A1* | 8/2002 | Ravichandran ...... | C07D 249/20 524/91 |
| 2005/0043541 A1 | 2/2005 | Walter et al. | |
| 2010/0063238 A1 | 3/2010 | Zhang et al. | |
| 2010/0162494 A1 | 7/2010 | Muller et al. | |
| 2010/0192312 A1 | 8/2010 | Cremer et al. | |

(Continued)

FOREIGN PATENT DOCUMENTS

| | | |
|---|---|---|
| CN | 101050223 | 10/2007 |
| CS | 215229 | 9/1981 |

(Continued)

OTHER PUBLICATIONS

Gao et al., Inorganic Chemistry (2007), 46(24), 10287-10293.*

(Continued)

*Primary Examiner* — Fereydoun G Sajjadi
*Assistant Examiner* — Kofi Adzamli
(74) *Attorney, Agent, or Firm* — Young & Thompson

(57) ABSTRACT

A novel compound represented by general formula (1), a support supporting this novel compound, and a photoelectric transduction element using this support. (In the formula, Y is an optionally substituted hydrocarbon group having 1-20 carbon atoms having —CO—NR4- or —SO$_2$—NR4- in the group; Z is a group of a conjugated system; R1, R2, and R3 represent optionally substituted hydrocarbon groups or optionally substituted hydrocarbon-oxy groups; at least one of R1, R2, and R3 is an optionally substituted hydrocarbon-oxy group; R4 represents a hydrogen atom or an optionally substituted hydrocarbon group having 1-20 carbon atoms; R4 and Z may join together to form a ring. However, Y excludes groups represented by partial structural formulas (Y-11) and (Y-12).)

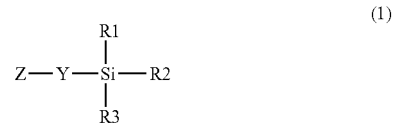

(1)

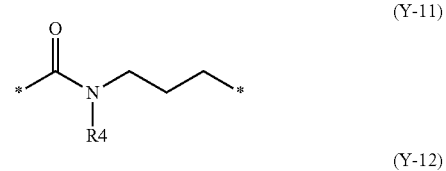

(Y-11)

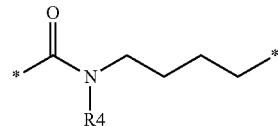

(Y-12)

11 Claims, 1 Drawing Sheet

(56) References Cited

U.S. PATENT DOCUMENTS

2012/0067249 A1    3/2012  Woods et al.

FOREIGN PATENT DOCUMENTS

| JP | 07-307133 | 11/1995 |
|---|---|---|
| JP | 2003-509513 | 3/2003 |
| JP | 2007-536527 | 12/2007 |
| JP | 2009-221059 | 10/2009 |
| JP | 2010-526897 | 8/2010 |
| JP | 2011-108527 | 6/2011 |
| JP | 2011-122088 | 6/2011 |
| JP | 2011-132163 | 7/2011 |
| WO | 03/006676 | 1/2003 |
| WO | 03-062253 | 7/2003 |
| WO | 2005/108625 | 11/2005 |
| WO | 2008-138726 | 11/2008 |
| WO | 2009/038659 | 3/2009 |
| WO | 2010/126920 | 11/2010 |

OTHER PUBLICATIONS

Coahuila Hernandez et al. Journal of Sol-Gel Science and Technology (2006), 37(2), 117-120.*
Gao et al., Inorganic Chemistry (2007), 46 (24), 10287-10293.*
International Search Report, PCT/JP2012/071093, Dec. 4, 2012.

* cited by examiner

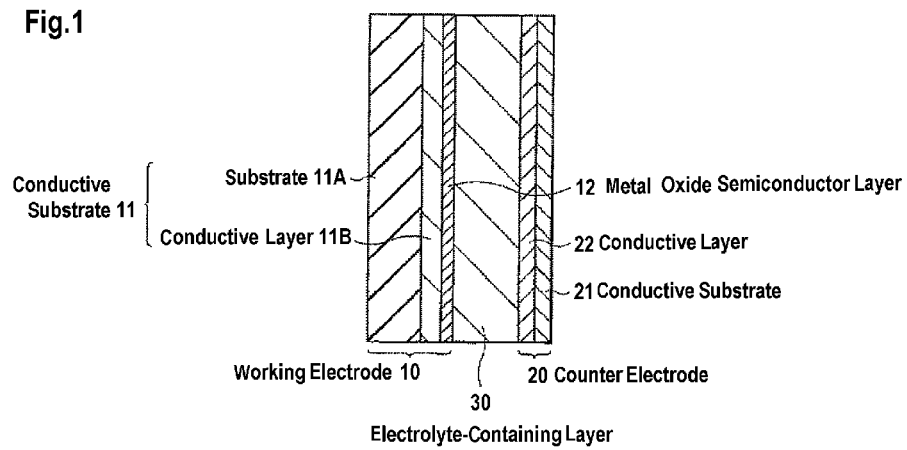
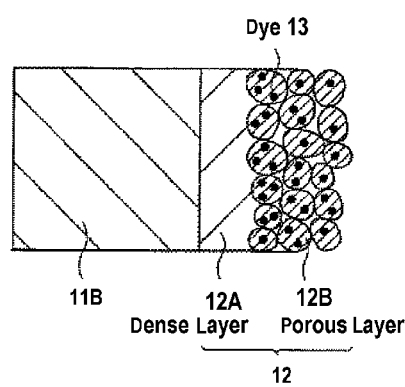

COMPOUND AND SUPPORT MATERIAL SUPPORTING THIS NOVEL COMPOUND

TECHNICAL FIELD

The invention relates to novel compounds, support materials carrying the novel compounds, and photoelectric conversion devices produced using the support materials.

BACKGROUND ART

Dyes have been widely used in a variety of technical fields. As an example in the field of photoelectric conversion devices such as solar cells, photosensitizing dyes are used in dye-sensitized photoelectric conversion devices. Such dye-sensitized photoelectric conversion devices are theoretically expected to have high efficiency and thought to be producible at a cost lower than that of traditional photoelectric conversion devices made with silicon semiconductors.

A dye-sensitized photoelectric conversion device has an electrode including an oxide semiconductor as a support on which a dye is supported. In such a dye-sensitized photoelectric conversion device, the dye is excited by absorbing incident light, and the excited dye injects electrons into the support to cause photoelectric conversion.

Techniques that have been studied to improve the conversion efficiency and durability of dye-sensitized photoelectric conversion devices include improvement in the dye's ability of being-supported on a support. Specifically, if physical or chemical adsorption ability of a dye to a support is increased, excited energy can be transferred with high efficiency from the dye to the support, and the dye can be prevented from leaching into the device (specifically, leaching into the electrolytic solution or the like). A technique of attaching a carboxyl group to dye molecules via an amide linkage (Patent Literature 1), a technique of attaching a reactive silyl group to a triarylamine (Patent Literature 2), etc. have been disclosed as techniques for improving the supporting ability.

Solar cells are one of the important applications of dye-sensitized photoelectric conversion devices. Such solar cells are required to have high durability because of the nature of the intended use, but known dyes and photoelectric conversion devices made with such dyes still have insufficient performance.

CITATION LIST

Patent Literature

Patent Literature 1: JP 2011-122088 A
Patent Literature 2: JP 2011-132163 A

SUMMARY OF THE INVENTION

Technical Problem

It is therefore an object of the invention to provide a novel compound, especially a novel compound as a dye having a high ability to adsorb to a support, to provide a support material carrying such a novel compound on a support, and to provide a photoelectric conversion device with high efficiency and high durability.

Solution to Problem

As a result of earnest study, the inventors have found novel compounds having a specific structure and have completed the invention based on the finding that the object can be achieved with such novel compounds.

Specifically, the invention provides a novel compound represented by formula (1) below,

[Chemical Formula 1]

$$Z-Y-\underset{\underset{R3}{|}}{\overset{\overset{R1}{|}}{Si}}-R2 \quad (1)$$

wherein
Y is an optionally substituted hydrocarbon group having 1 to 20 carbon atoms and having —CO—NR4- or —SO$_2$—NR4- in the group,
Z is a conjugated group,
R1, R2, and R3 each represent an optionally substituted hydrocarbon group or an optionally substituted hydrocarbonoxy group,
at least one of R1, R2, and R3 represents an optionally substituted hydrocarbonoxy group,
R4 represents a hydrogen atom or an optionally substituted hydrocarbon group having 1 to 20 carbon atoms,
R4 and Z may be linked together to form a ring,
provided that Y excludes the groups represented by partial structural formula (Y-11) and (Y-12),

[Chemical Formula 2]

(Y-11)

(Y-12)

wherein
R4 has the same definition as that of R4 described in formula (1),
any hydrogen atom in the formulae may be substituted with a fluorine atom, a chlorine atom, a bromine atom, an iodine atom, a cyano group, a nitro group, an —OR7 group, an —SR7 group, or an —NR7R8 group, and
any benzene ring in the formulae may be substituted with an aliphatic hydrocarbon group having 1 to 4 carbon atoms.

The invention also provides a support material carrying a compound represented by formula (1),

[Chemical Formula 3]

$$Z-Y-\underset{\underset{R3}{|}}{\overset{\overset{R1}{|}}{Si}}-R2 \quad (1)$$

wherein

Y is an optionally substituted hydrocarbon group having 1 to 20 carbon atoms and having —CO—NR4- or —SO$_2$—NR4- in the group, Z is a conjugated group, R1, R2, and R3 each represent an optionally substituted hydrocarbon group or an optionally substituted hydrocarbonoxy group, at least one of R1, R2, and R3 represents an optionally substituted hydrocarbonoxy group, R4 represents a hydrogen atom or an optionally substituted hydrocarbon group having 1 to 20 carbon atoms, and R4 and Z may be linked together to form a ring.

The invention also provides a photoelectric conversion device including an electrode having such a support material.

Effect of the Invention

The novel compound of the invention has high adsorption ability to a support because of its possession of a silyl group in which a hydrocarbonoxy group and a Si atom are bound together, and therefore, dye removal is suppressed in the support material of the invention carrying the novel compound, and the photoelectric conversion device produced using the support material is a device having high efficiency and high durability and is suitable for use in applications needed to have high durability, such as solar cells.

BRIEF DESCRIPTION OF THE DRAWINGS

FIG. 1 is a schematic diagram showing the cross-sectional structure of an example of the photoelectric conversion device of the invention.

FIG. 2 is an enlarged diagram of the principal part of the photoelectric conversion device of the invention shown in FIG. 1.

DESCRIPTION OF EMBODIMENTS

Hereinafter, the novel compound of the invention, the support material of the invention, and the photoelectric conversion device produced using the support material will be described with reference to preferred embodiments. As far as the compound represented by formula (1) shown in [Chemical Formula 3] given above carried by the support material of the invention is concerned, a compound in which Y is partial structural formula (Y-11) or (Y-12) is also used as a preferred compound as described below.

First, the novel compound of the invention and the support material of the invention will be described.

Examples of the material for use in the support material of the invention (hereinafter referred to as "support") include organic resins such as acrylic resins and fluororesins, metal oxides such as titanium oxide, zinc oxide, and aluminum oxide, silicon oxide, zeolite, activated carbon, etc., which preferably have a porous surface. The compound to be carried is characterized by being a compound represented by formula (1). The compound has high adsorption ability to a support because it has a silyl group in which a hydrocarbonoxy group and a Si atom are bound together. The compound can be supported on a support using a known method such as gas-phase adsorption or liquid-phase adsorption. An example of liquid-phase adsorption includes dissolving the compound of the invention in a solvent and immersing the support in the solution so that the compound may be adsorbed to the support.

The support may be in any shape. For example, the shape of the support may be appropriately selected from film shape, powdery shape, granular shape, or other shapes, depending on the intended use of the support material. The size of the support and the amount of the compound of the invention supported on the support are also not restricted, and they may be appropriately selected depending on the intended use of the support material.

The group represented by Y in formula (1) is a divalent group and specifically is an optionally substituted hydrocarbon group having 1 to 20 carbon atoms and having —CO—NR4- or —SO$_2$—NR4-.

Examples of the optionally substituted hydrocarbon group include a aliphatic hydrocarbon group, an unsubstituted aromatic hydrocarbon group, an aromatic hydrocarbon group substituted with at least one aliphatic hydrocarbon group, an unsubstituted heterocyclic group, and a heterocyclic group substituted with at least one aliphatic hydrocarbon group.

Examples of the divalent aliphatic hydrocarbon group include linear, branched, or cyclic aliphatic hydrocarbon groups and specifically include methane-1,1-diyl, ethane-1,2-diyl, 1-methylethane-1,2-diyl, propane-1,3-diyl, butane-1,4-diyl, 2-methylpropane-1,3-diyl, pentane-1,5-diyl, hexane-1,6-diyl, heptane-1,7-diyl, octane-1,8-diyl, nonane-1,9-diyl, decane-1,10-diyl, cyclohexane-1,4-diyl, etc. Especially, methane-1,1-diyl, ethane-1,2-diyl, and 1-methylethane-1,2-diyl are preferred because they will enhance the conversion efficiency of a photoelectric conversion device, which will be described below.

Examples of the divalent unsubstituted aromatic hydrocarbon group include 1,2-phenylene, 1,3-phenylene, 1,4-phenylene, etc.

Examples of the divalent unsubstituted heterocyclic group include furan-2,5-diyl, furan-3,5-diyl, thiophene-2,5-diyl, thiophene-3,5-diyl, 2H-chromene-3,7-diyl, benzothiophene-2,6-diyl, benzothiophene-2,5-diyl, etc.

Examples of the divalent aromatic hydrocarbon group substituted with at least one aliphatic hydrocarbon group include a group having one to three aliphatic hydrocarbon groups having 1 to 4 carbon atoms as substituents on the divalent unsubstituted aromatic hydrocarbon group. Examples of the divalent heterocyclic group substituted with at least one aliphatic hydrocarbon group include a group having one to three aliphatic hydrocarbon groups having 1 to 4 carbon atoms as substituents on the divalent unsubstituted heterocyclic group.

Examples of the aliphatic hydrocarbon group having 1 to 4 carbon atoms include linear, branched, or cyclic alkyl groups, such as methyl, ethyl, propyl, isopropyl, butyl, sec-butyl, tert-butyl, isobutyl, cyclopropyl, and cyclobutyl, and the aliphatic hydrocarbon group having 1 to 4 carbon atoms may be interrupted by —O—, —COO—, —OCO—, —CO—, —S—, —SO—, —SO$_2$—, —NR12-, —C═C—, or —C≡C—, wherein R12 is an aliphatic hydrocarbon group having 1 to 4 carbon atoms, examples of which are the same as those of the above-mentioned aliphatic hydrocarbon group having 1 to 4 carbon atoms. When the interrupting group has one or more carbon atom, the total number of carbon atoms including those in the interrupting group, is from 1 to 4.

The aliphatic hydrocarbon groups, the aromatic hydrocarbon groups or the heterocyclic groups listed above may further have a substituent(s). The aliphatic hydrocarbon groups, the aromatic hydrocarbon groups, and the heterocyclic groups may be substituted with groups such as a fluorine atom, a chlorine atom, a bromine atom, an iodine atom, a cyano group, a nitro group, an —OR7 group, an —SR7 group, and an —NR7R8 group. R7 and R8 represent the same groups as those represented by R7 and R8, respectively, in formulae (A2-1) to (A2-15) shown below. When the aliphatic hydrocarbon group, the aromatic hydrocarbon group, or the heterocyclic group has a methylene moiety, its two hydrogen atoms may be replaced by one oxygen atom to form carbonyl.

In the novel compound of the invention, specific examples of a preferred group represented by Y include groups represented by partial structural formulae (Y-1) to (Y-10). As far as the compound to be carried by the support material of the invention is concerned, specific examples of a preferred group represented by Y include groups represented by partial structural formulae (Y-11) and (Y-12) as well as partial structural formulae (Y-1) to (Y-10). R4 in each of formulae (Y-1) to (Y-10), (Y-11), and (Y-12) is the same as that described for formula (1), wherein any hydrogen atom may be substituted with the above-described aliphatic hydrocarbon group, aromatic hydrocarbon group, or heterocyclic group, and any benzene ring in the formulae may be substituted with the above-described aliphatic hydrocarbon group having 1 to 4 carbon atoms.

[Chemical Formula 4]

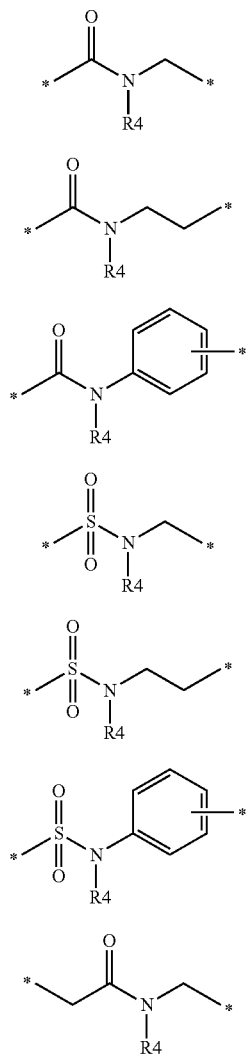

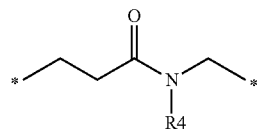

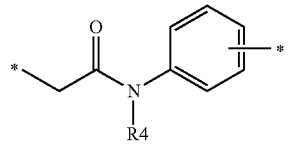

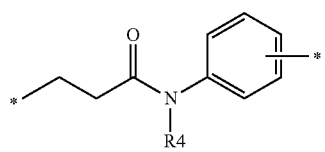

[Chemical Formula 5]

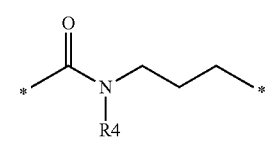

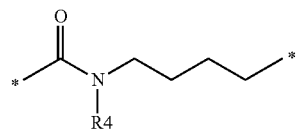

Z is not particularly restricted as far as it is a π conjugated group, and it may have a substituent. In the invention, it is preferred that the π conjugated group represented by Z contains a nitrogen atom or that the substituent attached to Z is an amino group. In the invention, the term "π conjugated group" means to be formed from unsaturated bonds linked in series. In the π conjugated groups represented by Z, the number of carbon atoms of the unsaturated bonds formed in series is preferably 4 to 60, more preferably 12 to 40, from the viewpoint that the conversion efficiency of a photoelectric conversion device described below is thereby increased successfully. When Z has a plurality of nitrogen atoms, the smallest number of the linked unsaturated bond carbon atoms is in the preferred range shown above.

Specific examples of a preferred π conjugated group represented by Z include groups represented by partial structural formula (2),

[Chemical Formula 6]

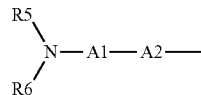

wherein
A1 represents an optionally substituted aromatic hydrocarbon ring group or an optionally substituted aromatic heterocyclic group,
A2 represents a direct bond or a group comprising a chain of one to seven pieces of one or more groups selected from groups represented by formulae (A2-1) to (A2-15) below, R5 and R6 each represent an optionally substituted hydrocarbon group, R5 and R6 may be linked together to form a ring, and R5 and R6 may be each independently linked with A1 to form a ring,

[Chemical Formula 7]

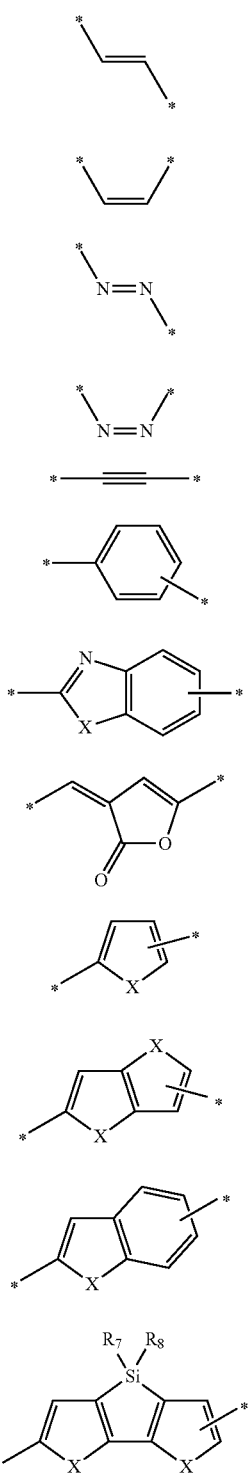

(A2-1)
(A2-2)
(A2-3)
(A2-4)
(A2-5)
(A2-6)
(A2-7)
(A2-8)
(A2-9)
(A2-10)
(A2-11)
(A2-12)

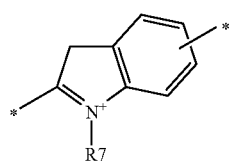

(A2-13)

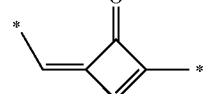

(A2-14)

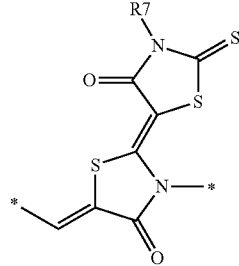

(A2-15)

wherein

X represents S, O, or NR,

R represents a hydrogen atom or an optionally substituted hydrocarbon group, and any hydrogen atoms in the formulae may be substituted with a fluorine atom, a chlorine atom, an iodine atom, a cyano group, a nitro group, an —OR7 group, an —SR7 group, an —NR7R8 group, or an optionally substituted aliphatic hydrocarbon group, wherein R7 and R8 each represent a hydrogen atom or an optionally substituted hydrocarbon group.

In partial structural formula (2), the group represented by A1 is a divalent group which is an optionally substituted aromatic hydrocarbon ring group or an optionally substituted aromatic heterocyclic group.

Examples of the aromatic hydrocarbon ring group include an unsubstituted aromatic hydrocarbon ring group, an aliphatic hydrocarbon group-substituted aromatic hydrocarbon ring group, etc. Examples of the aromatic heterocyclic group include an unsubstituted aromatic heterocyclic group, an aliphatic hydrocarbon group-substituted aromatic heterocyclic group, etc.

Examples of the divalent unsubstituted aromatic hydrocarbon ring group include 1,2-phenylene, 1,3-phenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, anthracene-1,4-diyl, anthracene-1,5-diyl, anthracene-1,10-diyl, anthracene-9,10-diyl, perylene-3-10-diyl, perylene-3,10-diyl, pyrene-1,6-diyl, pyrene-2,7-diyl, etc.

For example, the aliphatic hydrocarbon group-substituted divalent aromatic hydrocarbon ring group may have one to three aliphatic hydrocarbon groups of 1 to 20 carbon atoms as substituents on the divalent unsubstituted aromatic hydrocarbon ring.

Examples of the aliphatic hydrocarbon group of 1 to 20 carbon atoms include linear, branched, and cyclic alkyl groups such as methyl, ethyl, propyl, isopropyl, butyl, sec-butyl, tert-butyl, isobutyl, amyl, isoamyl, tert-amyl, hexyl, heptyl, isoheptyl, tert-heptyl, n-octyl, isooctyl, tert-octyl, nonyl, cyclopropyl, cyclobutyl, cyclopentyl, cyclohexyl, cycloheptyl, cyclooctyl, cyclononyl, and cyclodecyl. The aliphatic hydrocarbon group of 1 to 20 carbon atoms may be interrupted by —O—, —COO—, —OCO—, —CO—, —S—, —SO—, —SO$_2$—, —NR13-, —C=C—, or —C≡C—, wherein R13 is an aliphatic hydrocarbon group of 1 to 20 carbon atoms, which may be exemplified by the same groups as the above aliphatic hydrocarbon group of 1 to 20 carbon atoms. When the interrupting group has one or more carbon atom, the total number of carbon atoms including those in the interrupting group, is from 1 to 20.

Examples of the divalent unsubstituted aromatic heterocyclic group include furan-2,5-diyl, furan-3,5-diyl, thiophene-2,5-diyl, thiophene-3,5-diyl, 2H-chromene-3,7-diyl, benzothiophene-2,6-diyl, benzothiophene-2,5-diyl, etc.

Examples of the aliphatic hydrocarbon group-substituted divalent aromatic heterocyclic group include 1-alkyl-pyrrole-2,5-diyl, 1-alkyl-pyrrole-3,5-diyl, and a group having one to three aliphatic hydrocarbon groups of 1 to 20 carbon atoms as substituents on the divalent unsubstituted aromatic heterocyclic group. The aliphatic hydrocarbon group of 1 to 20 carbon atoms may be exemplified by the same groups as the above aliphatic hydrocarbon group of 1 to 20 carbon atoms.

The aromatic hydrocarbon ring groups or the aromatic heterocyclic groups listed above may further have a substituent(s). The aromatic hydrocarbon ring groups and the aromatic heterocyclic groups may be substituted with groups such as a fluorine atom, a chlorine atom, a bromine atom, an iodine atom, a cyano group, a nitro group, a hydroxyl group, a thiol group, and an —NR7R8 group. R7 and R8 represent the same groups as those represented by R7 and R8, respectively, in formulae (A2-1) to (A2-12) shown above. When the aromatic hydrocarbon ring group or the aromatic heterocyclic group has a methylene moiety, its two hydrogen atoms may be replaced by one oxygen atom to form carbonyl.

A2 in partial structural formula (2) represents a direct bond or a group comprising a chain of one to seven, preferably two to four, pieces of one or more groups selected from groups represented by formulae (A2-1) to (A2-15) shown above. Pieces of each group represented by any of formulae (A2-1) to (A2-15) may be linked in any direction. The mark * in the group represented by each of formulae (A2-1) to (A2-15) indicates the position to which the adjacent group is to be linked (the same applies hereinafter).

In formulae (A2-1) to (A2-15), X represents S, O, or NR, wherein R represents a hydrogen atom or an optionally substituted hydrocarbon group. Examples of the optionally substituted hydrocarbon group represented by R are the same as those of the optionally substituted hydrocarbon group represented by R1, R2, and R3 described below.

Any hydrogen atom in the groups represented by formulae (A2-1) to (A2-15) may be substituted with a fluorine atom, a chlorine atom, a bromine atom, an iodine atom, a cyano group, a nitro group, an —OR7 group, an —SR7 group, an —NR7R8 group, or an optionally substituted aliphatic hydrocarbon group, wherein R7 and R8 each represent a hydrogen atom or an optionally substituted hydrocarbon group. Groups as substituents on the A2 group may be linked together to form a ring.

For example, the optionally substituted aliphatic hydrocarbon group may be the above aliphatic hydrocarbon group of 1 to 20 carbon atoms, and the groups may be substituted with the groups listed above as substituents for the aromatic hydrocarbon ring group and the aromatic heterocyclic group.

Examples of the optionally substituted hydrocarbon groups represented by R7 and R8 are the same as those of the optionally substituted hydrocarbon groups represented by R1, R2, and R3 described below.

Examples of the structure of the A1-A2 moiety in partial structural formula (2) include A(1) to A(36) shown below. In each of the examples of the A1-A2 moiety shown below, the ring structure at the left end corresponds to A1, and the other part corresponds to A2.

Although the examples shown below have no substituents, the A1 moiety may have a substituent(s) and any hydrogen atom in the A2 moiety may be substituted with a substituent as described above. In each of A(16) to A(23) shown below, each bond drawn across two or more rings means that the bond may be attached to any of the carbon atoms in these rings (the same applies hereinafter).

[Chemical Formula 8]

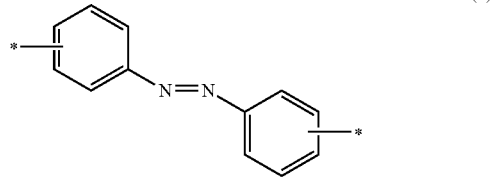

A(1)

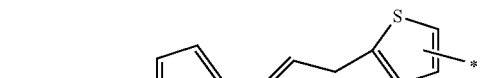

A(2)

A(3)

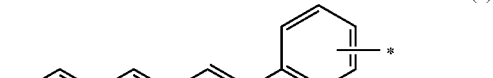

A(4)

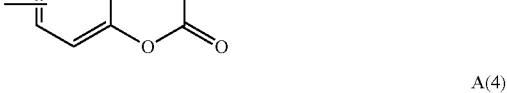

A(5)

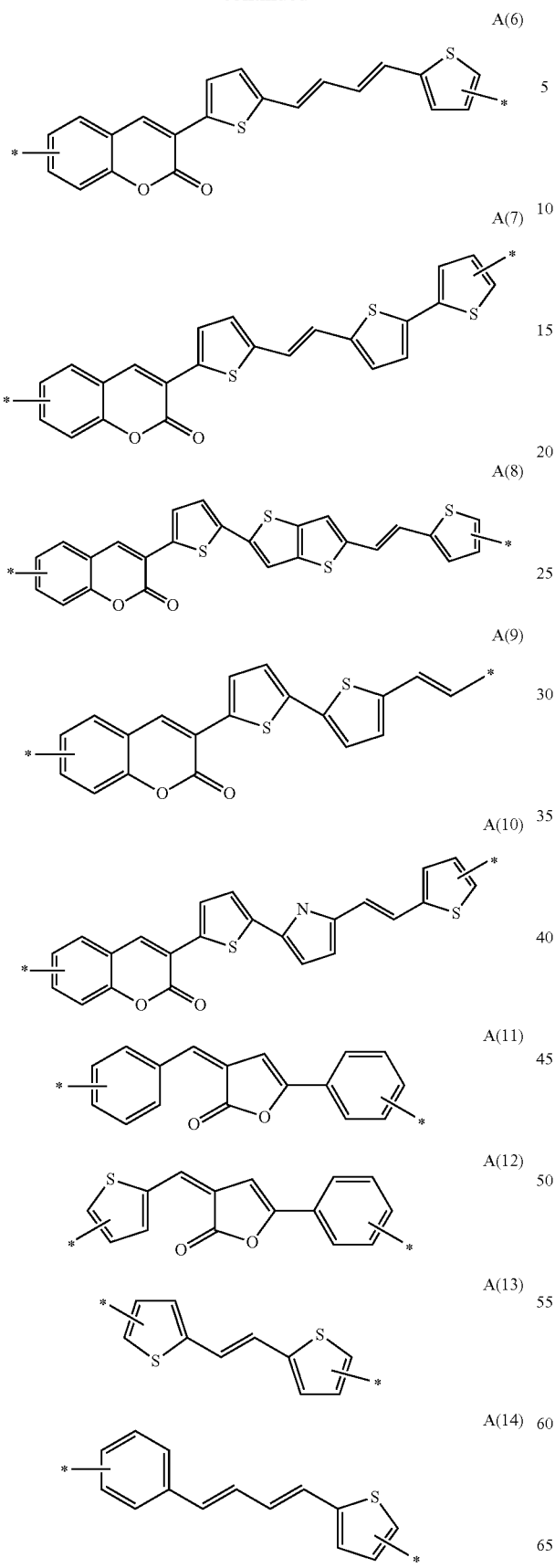
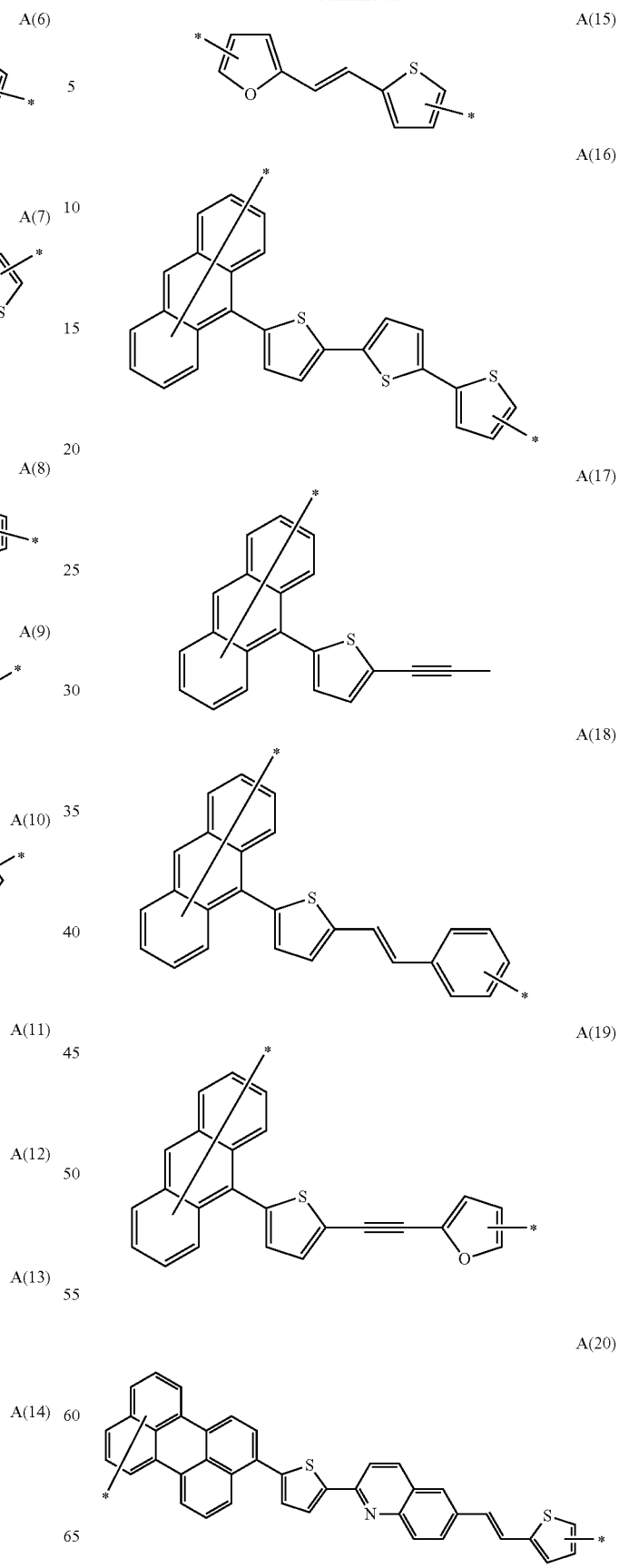

-continued
A(21)
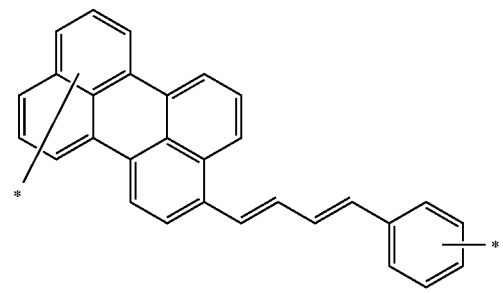
A(22)
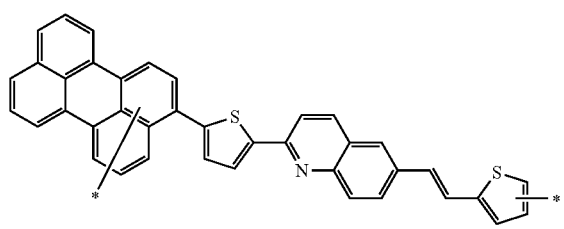
A(23)
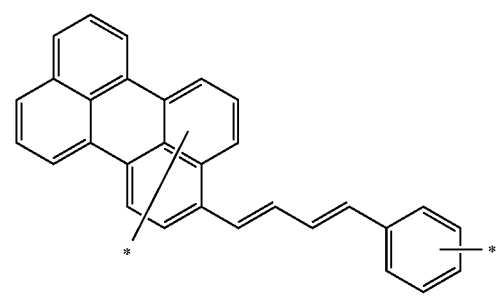
A(24)
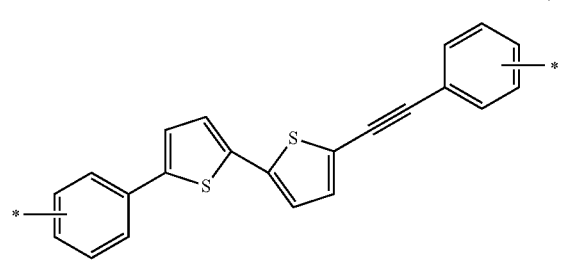
A(25)
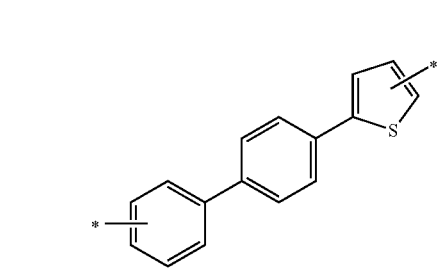
A(26)
-continued
A(27)
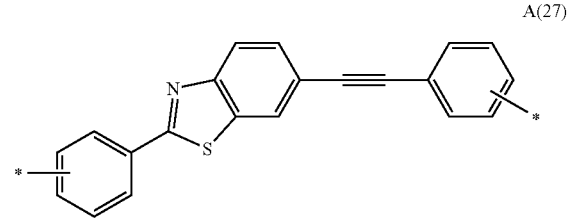
A(28)
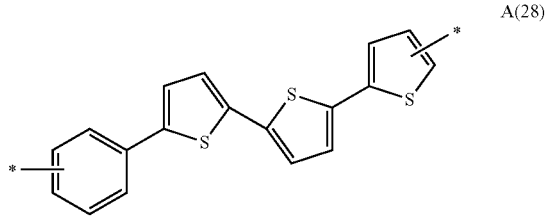
A(29)
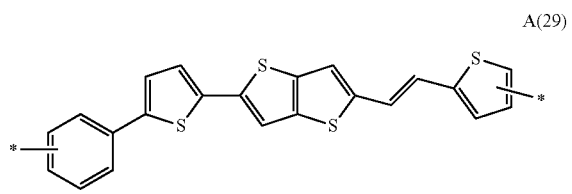
A(30)
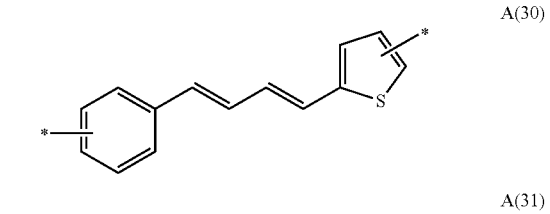
A(31)
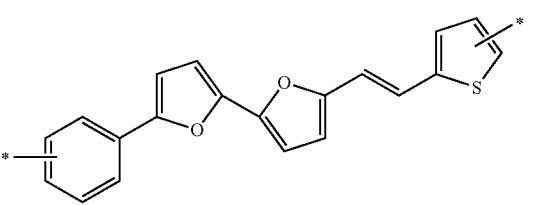
A(32)
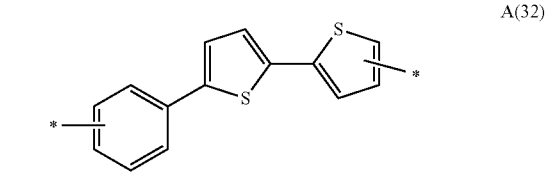
A(33)
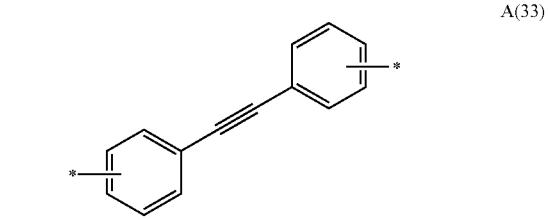
A(34)
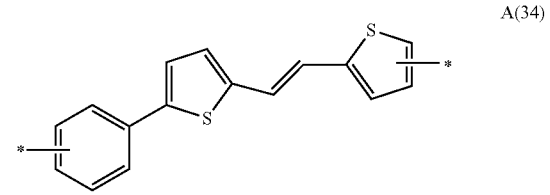

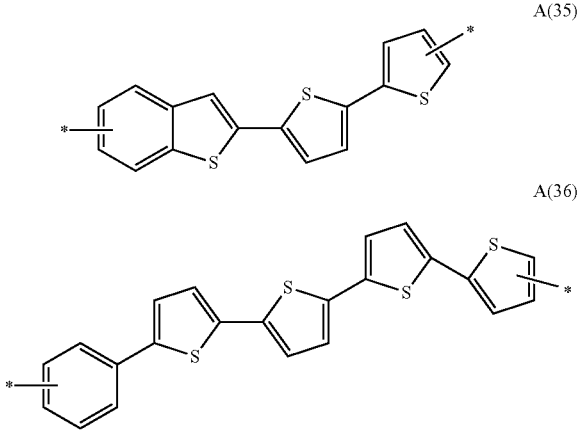

In formula (1), the hydrocarbon group of the optionally substituted hydrocarbon group represented by R1, R2, and R3 may be an aromatic hydrocarbon group, an aliphatic hydrocarbon group-substituted aromatic hydrocarbon group, an aliphatic hydrocarbon group, or the like.

The aromatic hydrocarbon group may be phenyl, naphthyl, cyclohexylphenyl, biphenyl, terphenyl, fluorenyl, thiophenylphenyl, furanylphenyl, 2'-phenyl-propylphenyl, benzyl, naphthylmethyl, or the like. Examples of the aliphatic hydrocarbon group include the aliphatic hydrocarbon groups having 1 to 20 carbon atoms described for A1. The aliphatic hydrocarbon group-substituted aromatic hydrocarbon group may be phenyl, naphthyl, benzyl or the like substituted with the aliphatic hydrocarbon group.

These hydrocarbon groups may be substituted with a substituent such as a fluorine atom, a chlorine atom, a bromine atom, an iodine atom, a cyano group, a nitro group, a hydroxyl group, a thiol group, or an —NR7R8 group, wherein R7 and R8 represent the same groups as R7 and R8 described above for A2.

In formula (1), the optionally substituted hydrocarbonoxy group represented by R1, R2, and R3 may has an optionally substituted hydrocarbon moiety, which can be exemplified by the same groups as the optionally substituted hydrocarbon group represented by R1 described above, and an —O— moiety, which is interposed between the hydrocarbon moiety and the Si atom.

At least one of R1, R2, and R3 represents an optionally substituted hydrocarbonoxy group. In terms of the high ability to adsorb to the support described below, it is preferable that at least one of R1, R2, and R3 is an aliphatic hydrocarbonoxy group, or all of R1, R2, and R3 are optionally substituted hydrocarbonoxy groups. It is more preferable that two or three of R1, R2, and R3 are each a linear or branched aliphatic hydrocarbonoxy group (especially of 1 to 5 carbon atoms), and none or one of them is a linear or branched aliphatic hydrocarbon group (especially of 1 to 5 carbon atoms). It is most preferable that all of R1, R2, and R3 are each a linear or branched aliphatic hydrocarbonoxy group (especially of 1 to 5 carbon atoms).

Examples of the optionally substituted hydrocarbon group represented by R5 and R6 may be the same groups described above as those of the hydrocarbon group represented by R1. R5 and R6 may be linked together to form a ring, or/and R5 and R6 may each independently be linked with A to form a ring.

Of the compounds represented by formula (1), compounds in which the partial structure (3) shown below is any one of the partial structures (3-1) to (3-12) shown below are preferred because they exhibit particularly good properties for photoelectric conversion applications. The compound having the partial structure (3-1), (3-2), or (3-10) shown below is particularly preferred because it is easy to produce and has high efficiency of electron injection into the support.

In the partial structures (3) and (3-1) to (3-12) shown below, a mark of the bond of A1 to A2 is not shown. In the partial structures (3-1) to (3-12) shown below, the bond of A1 to A2 may be attached to any carbon atom of the aromatic hydrocarbon ring and the aromatic heterocyclic ring.

[Chemical Formula 9]

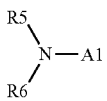

(3)

wherein A1, R5, and R6 are the same as those of partial structural formula (2),

[Chemical Formula 10]

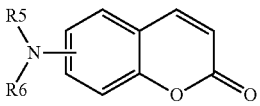

(3-1)

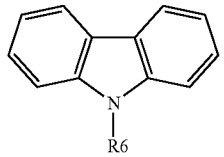

(3-2)

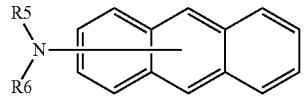

(3-3)

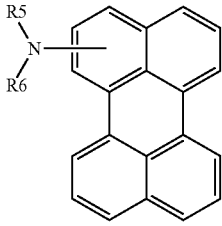

(3-4)

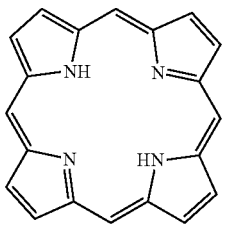

(3-5)

-continued (3-6)

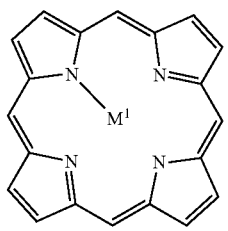

(3-7)

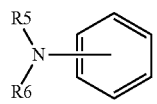

(3-8)

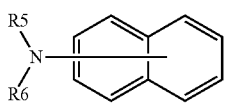

(3-9)

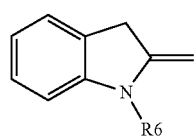

(3-10)

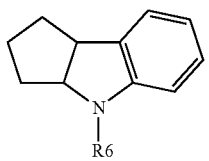

(3-11)

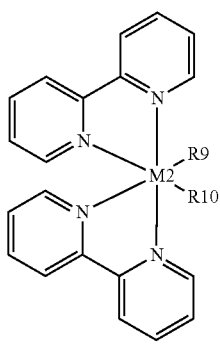

(3-12)

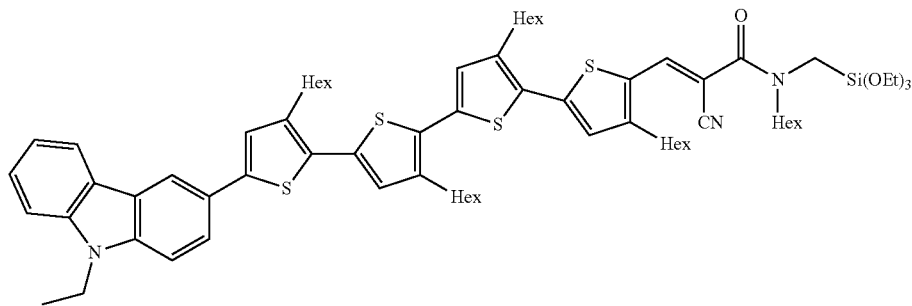

wherein

R5 and R6 are the same as those of partial structural formula (2),

R9, R10, and R11 each represent a known ligand that coordinates to M2,

M1 and M2 each represents a metal element, and any hydrogen atoms in the formulae may be substituted with a fluorine atom, a chlorine atom, an iodine atom, a cyano group, a nitro group, an —OR7 group, an —SR7 group, or an optionally substituted aliphatic hydrocarbon group, wherein R7 and R8 each represent a hydrogen atom or an optionally substituted hydrocarbon group.

In (3-6), which represents the partial structure (3), specific examples of the metal element of M1 include Mg, Ca, Sr, Ba, Sc, Y, La, Ce, Pr, Nd, Sm, Eu, Gd, Tb, Dy, Ho, Sn, Yb, Ti, Zr, Hf, V, Nb, Ta, Th, U, Mn, Cu, Cr, Fe, Co, Zn, Mo, Ni, and Rh; of these, Cu, Ti, Ni, Fe, and Zn are preferred, and Cu or Zn is more preferred.

In (3-11) and (3-12), which represent the partial structure (3), examples of the metal element of M2 include metals capable of forming tetra-coordination or hexa-coordination; Ru, Fe, Os, Cu, W, Cr, Mo, Ni, Pd, Pt, Co, Ir, Rh, Re, Mn, and Zn are more preferred, Ru, Fe, Os, and Cu are even more preferred, and Ru is particularly preferred.

In (3-11) and (3-12), which represent the partial structure (3), the known ligand that coordinates to M2 represented by R9, R10, or R11 is a unidentate, bidentate, or tridentate ligand, and the ligand may be either a neutral ligand or an anionic ligand. While specific ligands are not particularly restricted, halogen atoms, —NCS, oxalic acid, etc. are preferred and halogen atoms and —NCS are more preferred.

Specific examples of the novel compound represented by formula (1) include, but are not limited to, compounds Nos. 1 to 73 shown below. In the formula, Me represents a methyl group, Et represents an ethyl group, Pr represents a propyl group, Bu represents a butyl group, Hex represents a hexyl group, Oct represents an octyl group, Non represents a nonyl group, Dec represents a decyl group, and TBA represents a tetrabutylammonium group.

[Chemical Formula 11]

No. 1

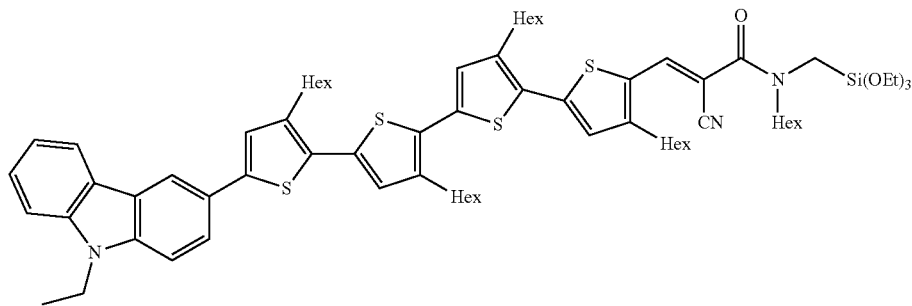

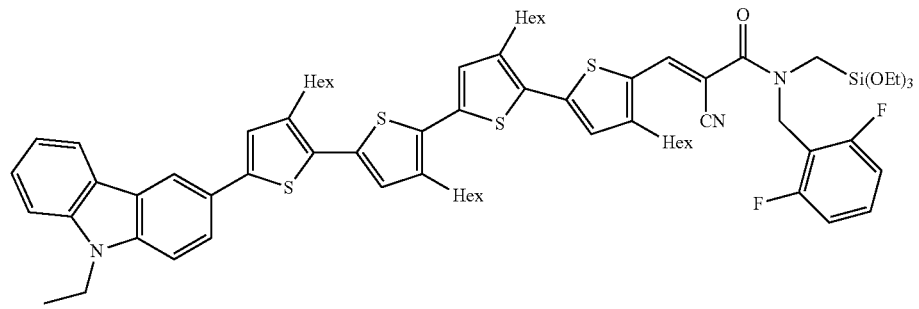
No. 2
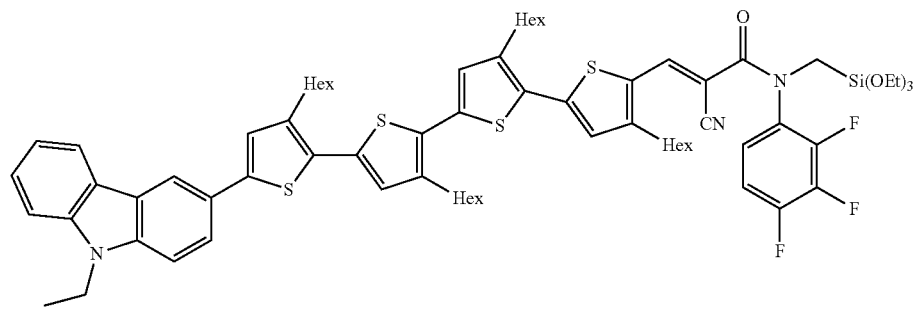
No. 3
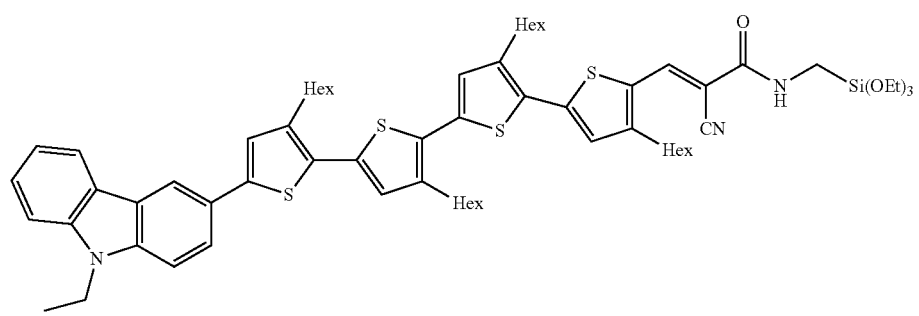
No. 4
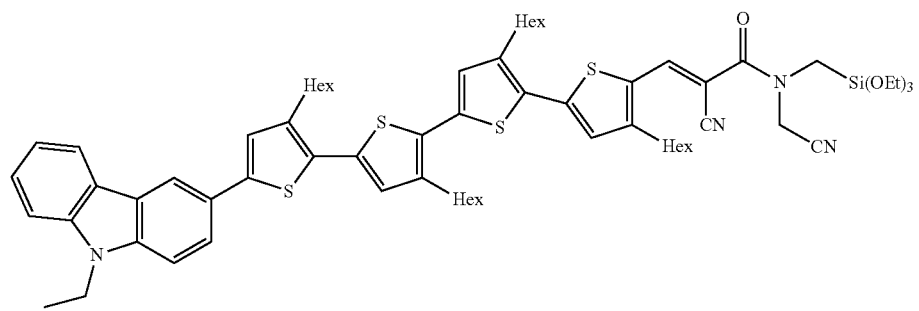
No. 5
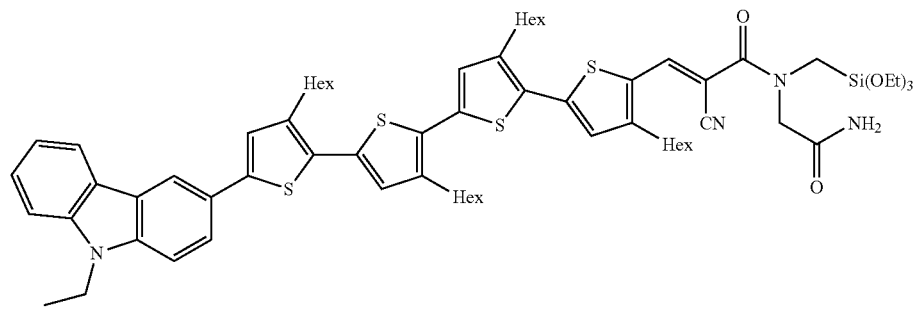
No. 6

-continued
No. 7
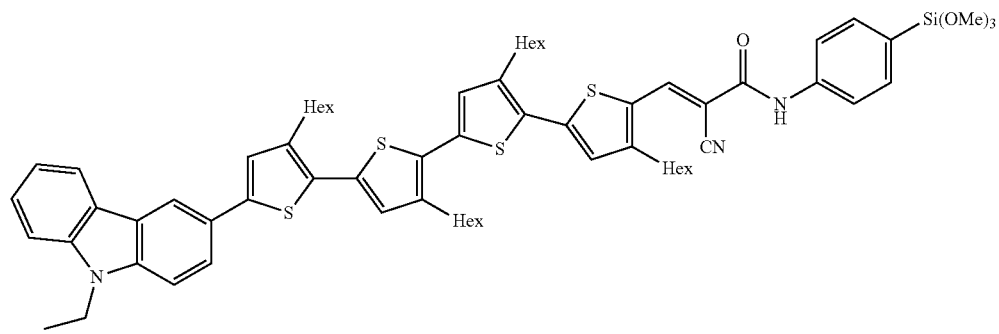
No. 8
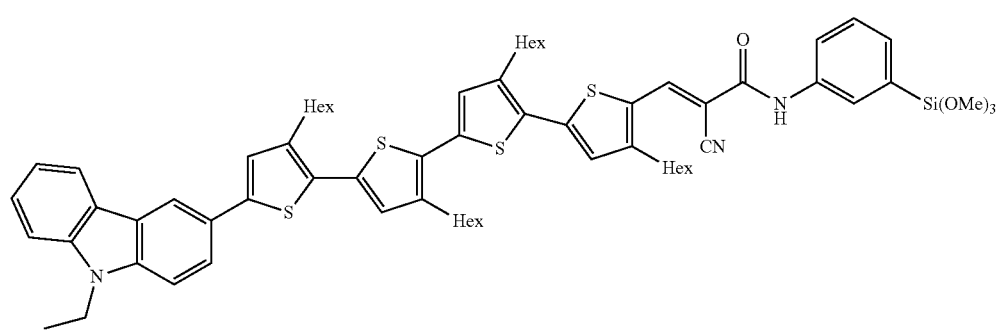
No. 9
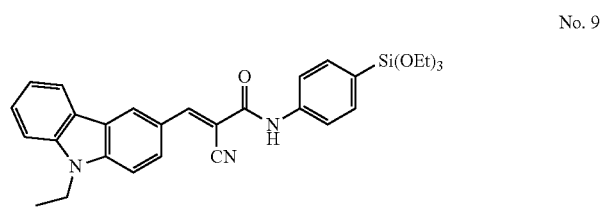
No. 10
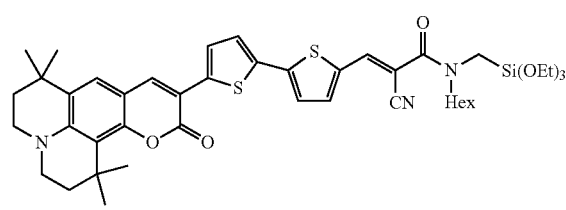
No. 11
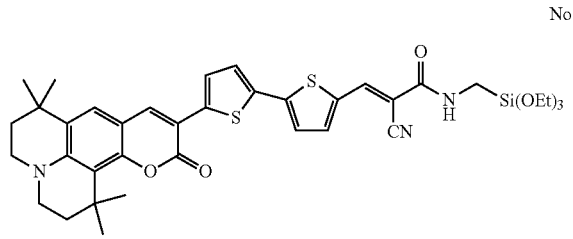
No. 12
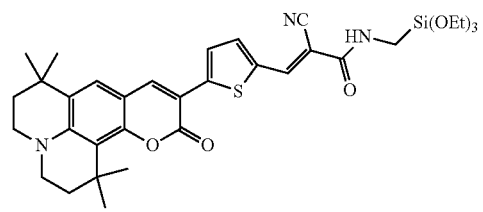
No. 13
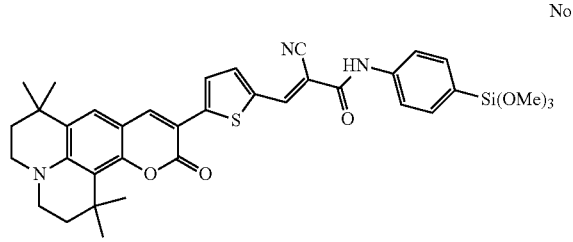
No. 14
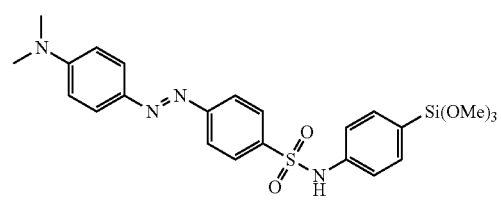

[Chemical Formula 12]
No. 15
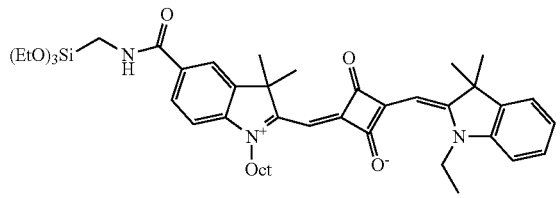
No. 16
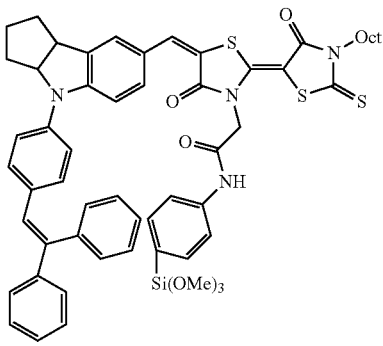
No. 17
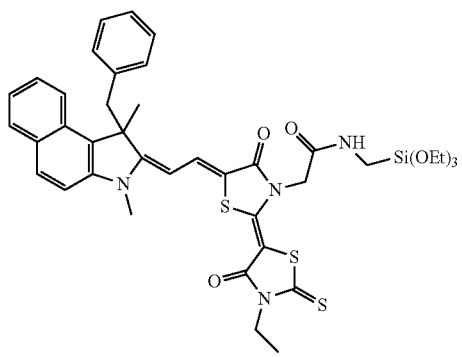
No. 18
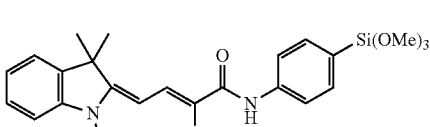
No. 19
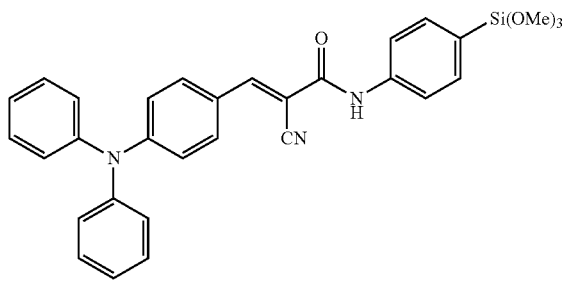
No. 20
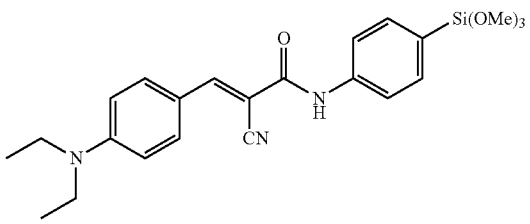
No. 21
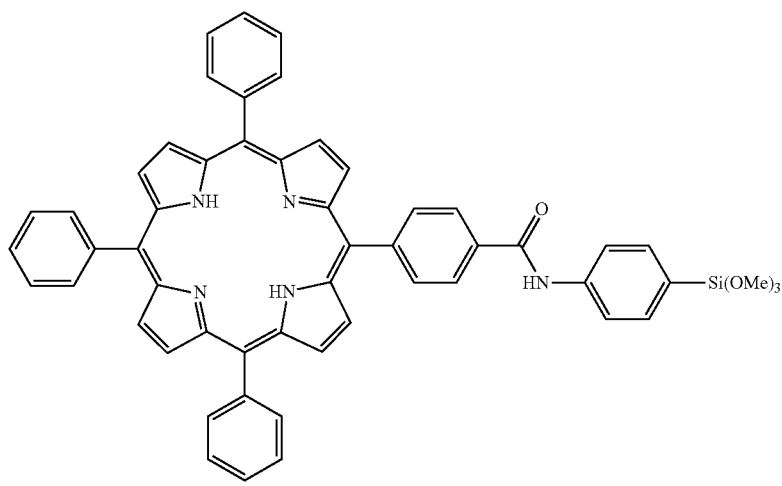

-continued
No. 22
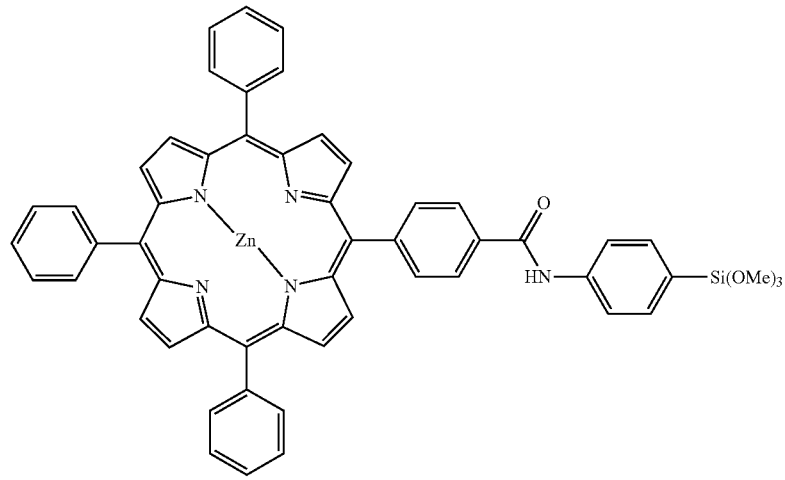
[Chemical Formula 13]
No. 23
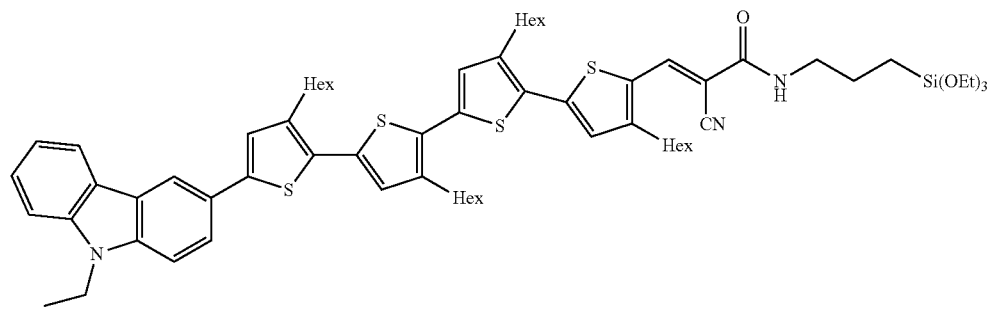
No. 24
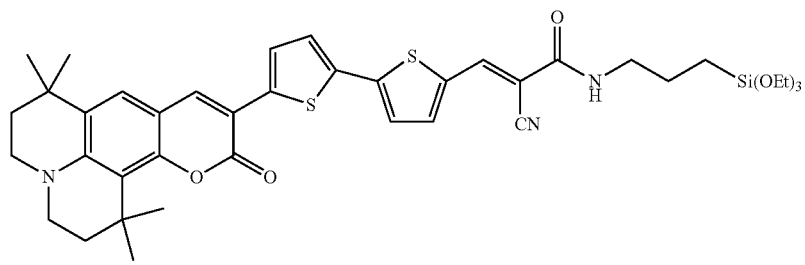
No. 25
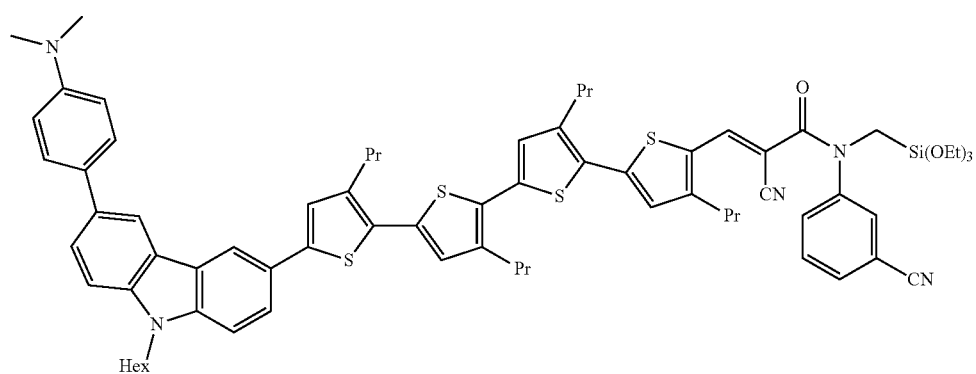

-continued
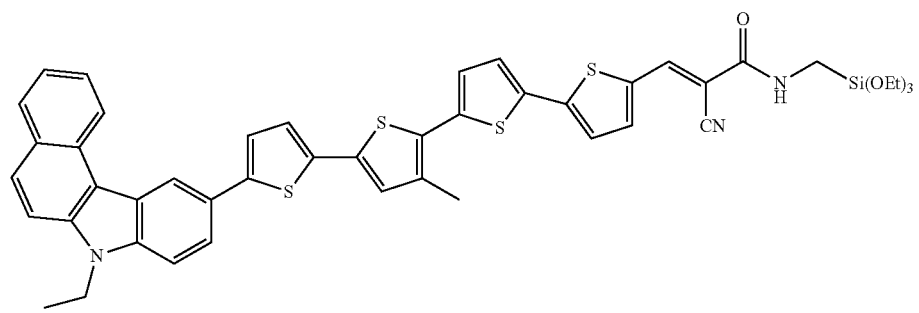
No. 26
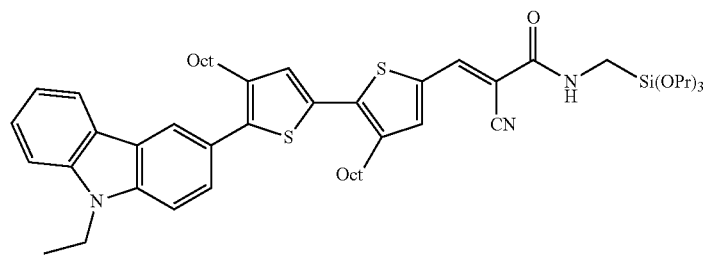
No. 27
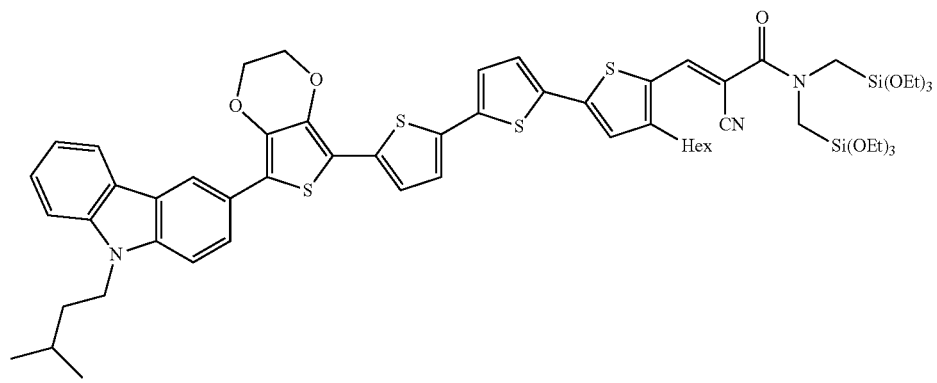
No. 28
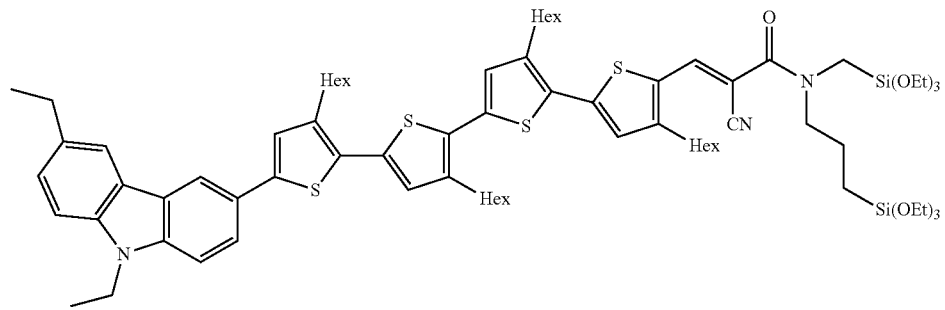
No. 29
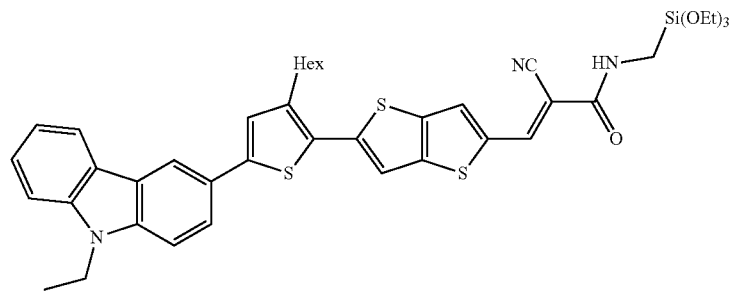
No. 30

-continued
No. 31
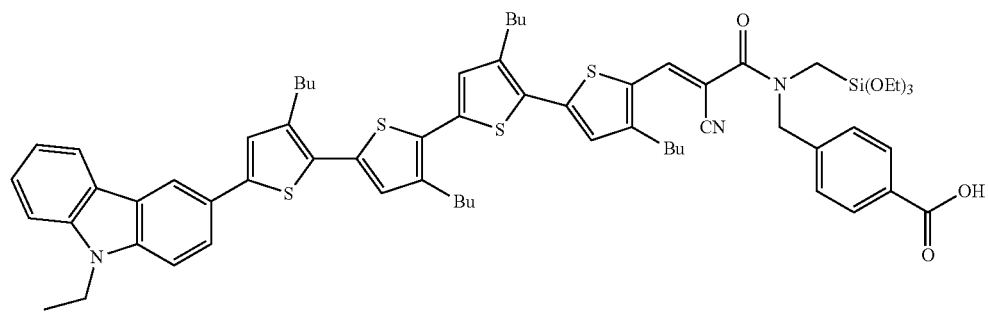
No. 32
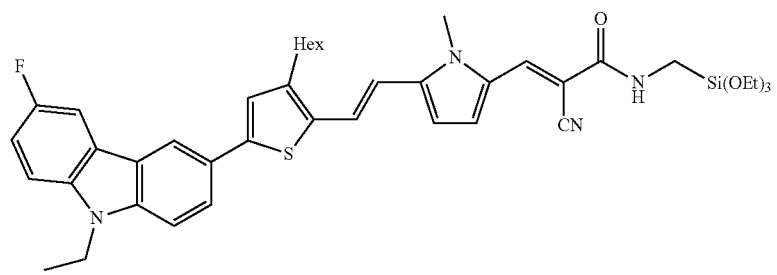
No. 33
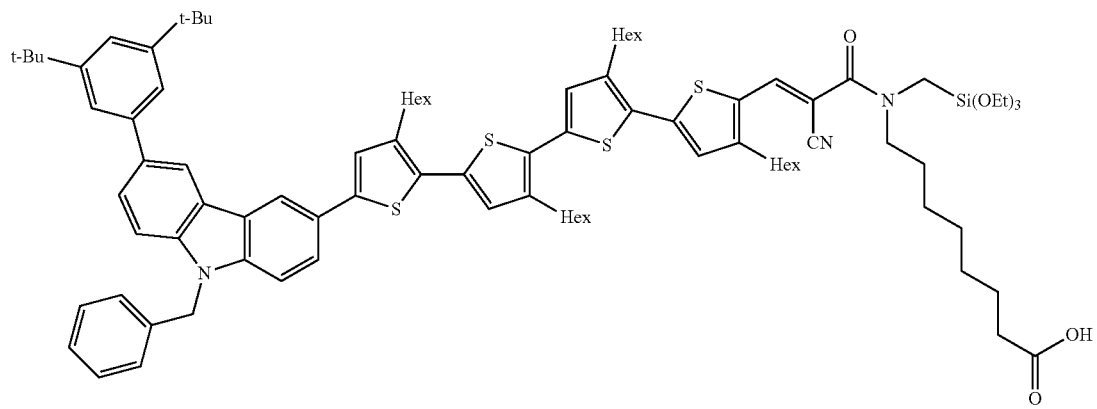
No. 34
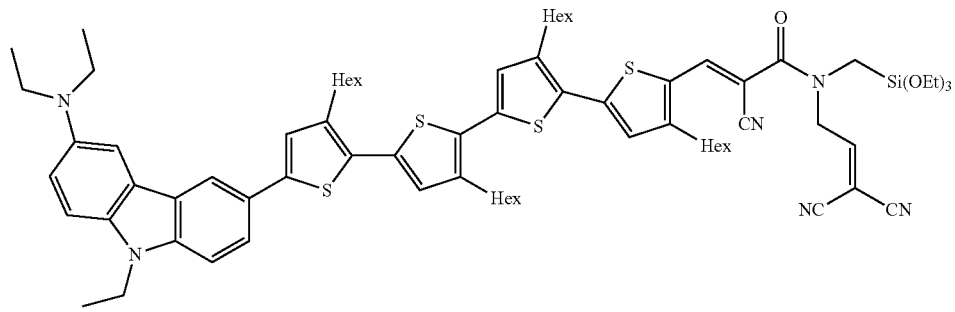
No. 35
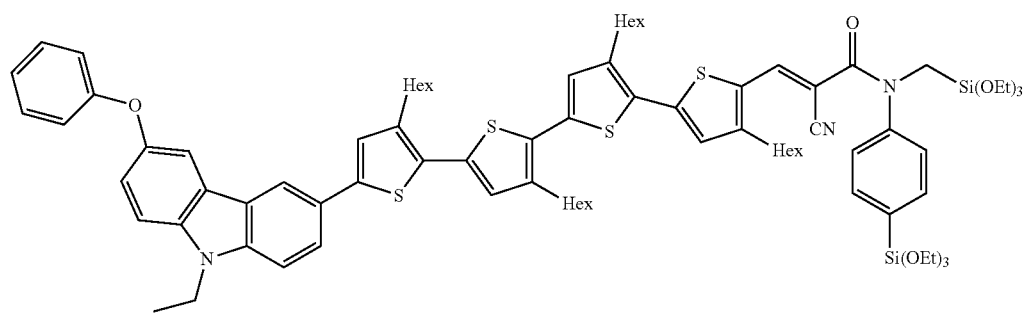

-continued
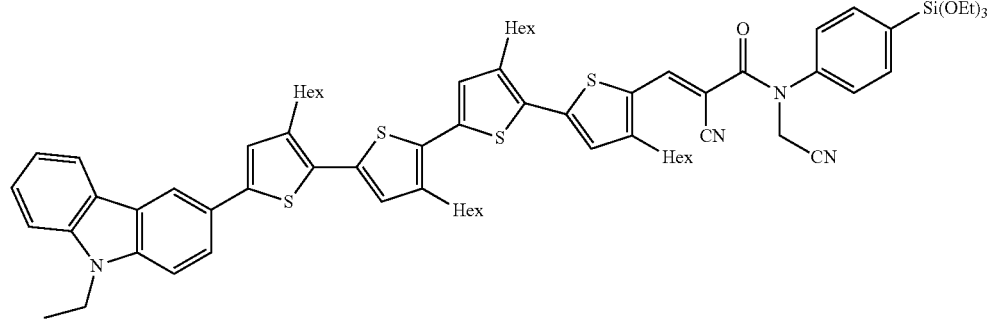
No. 36
[Chemical Formula 14]
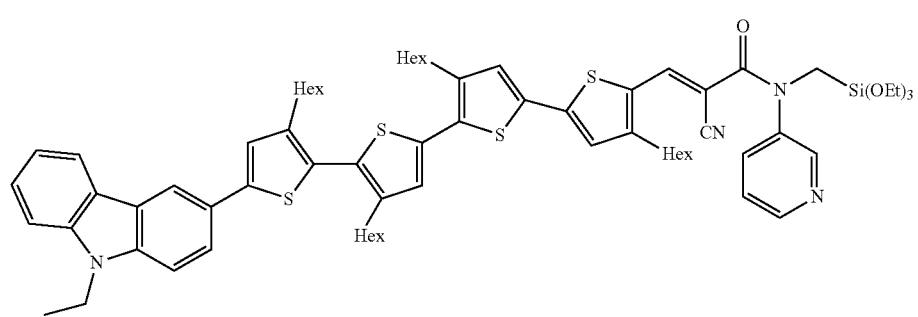
No. 37
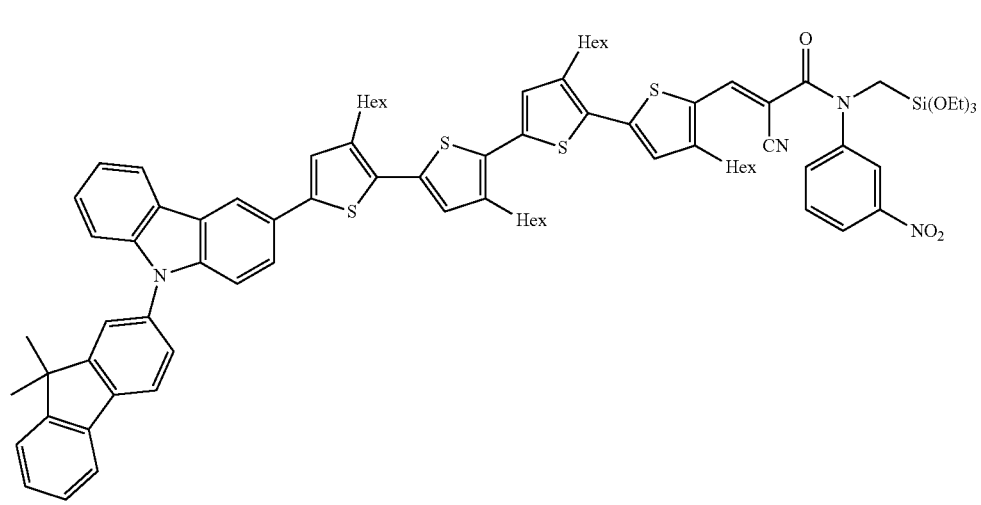
No. 38
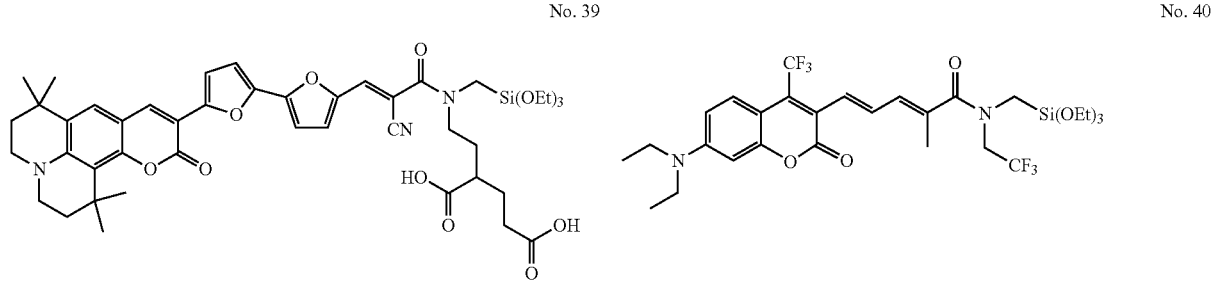
No. 39       No. 40

No. 41
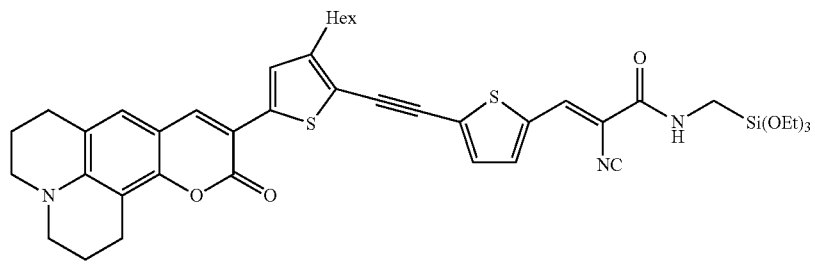
No. 42
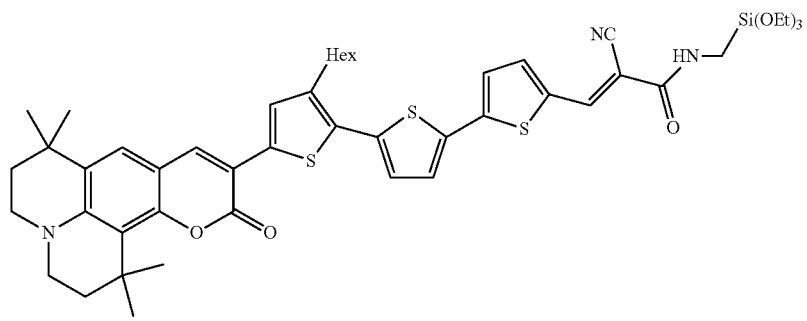
No. 43
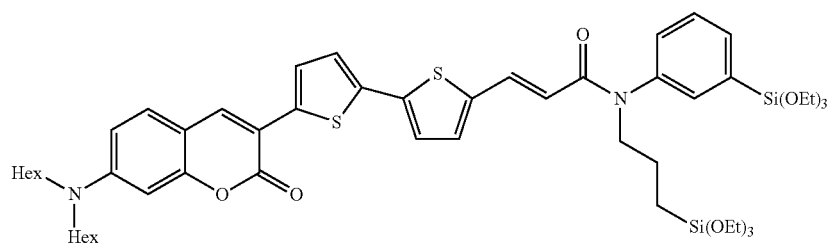
No. 44 No. 45
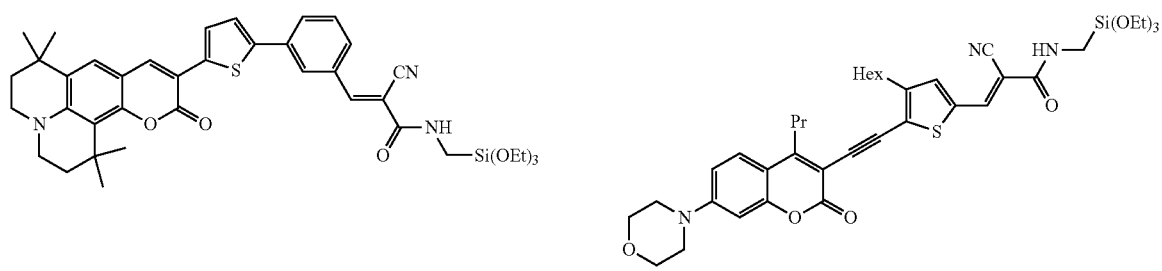
No. 46
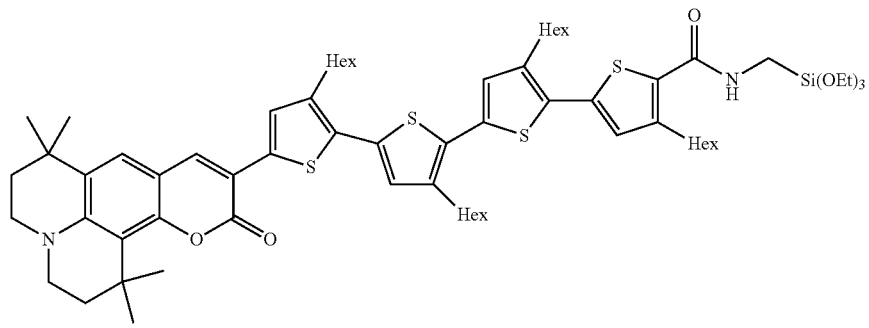

-continued
No. 47
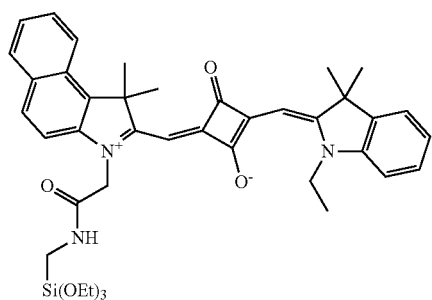
No. 48
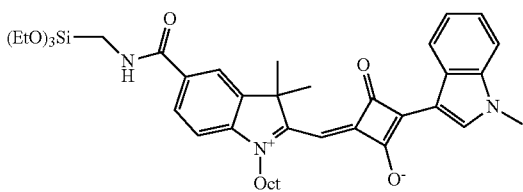
No. 49
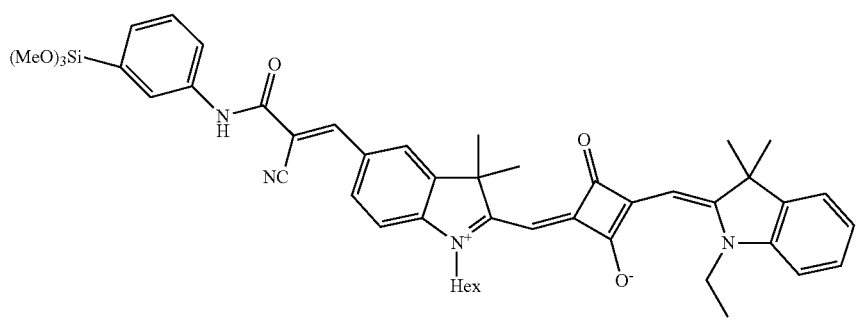
[Chemical Formula 15]
No. 50
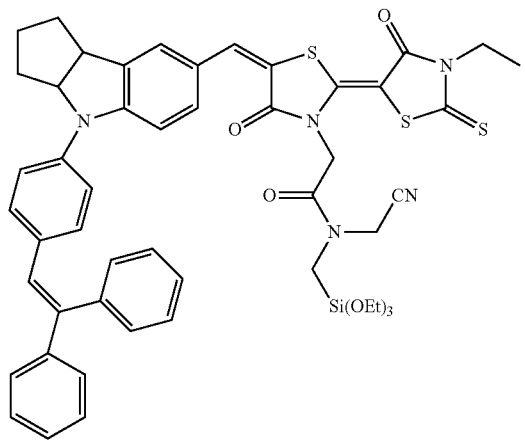
No. 51
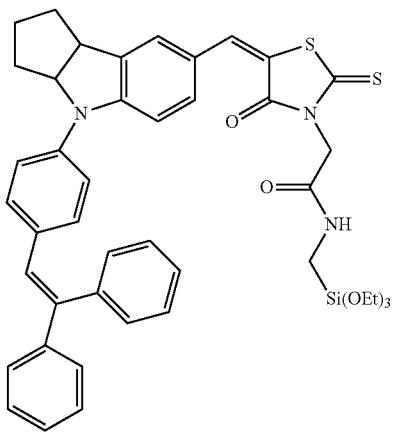
No. 52
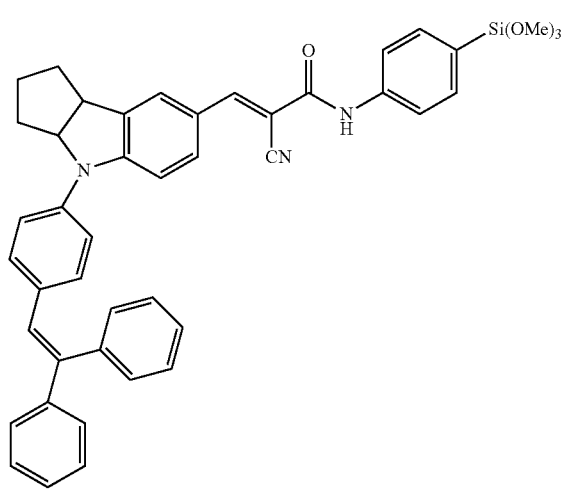
No. 53
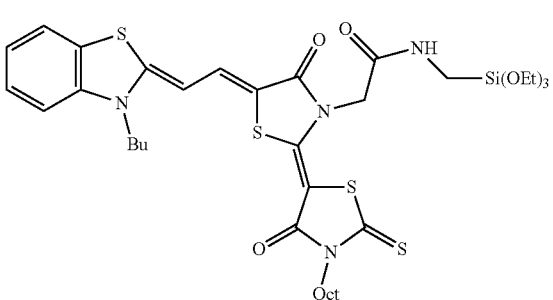

-continued
No. 54
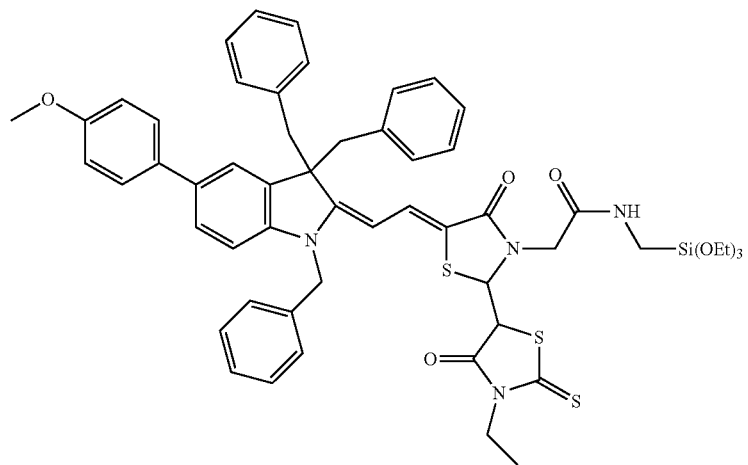
No. 55
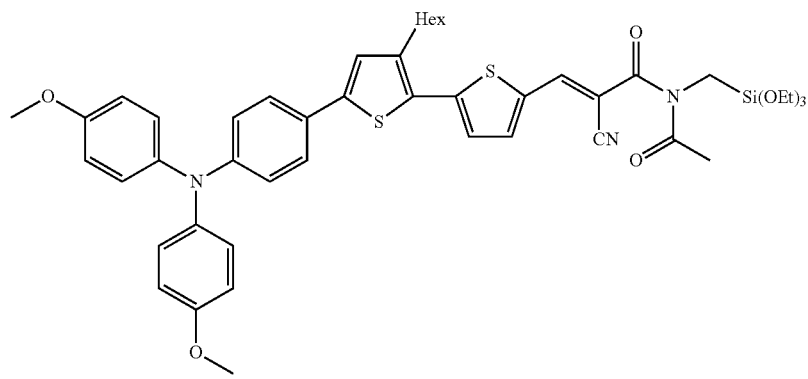
No. 56
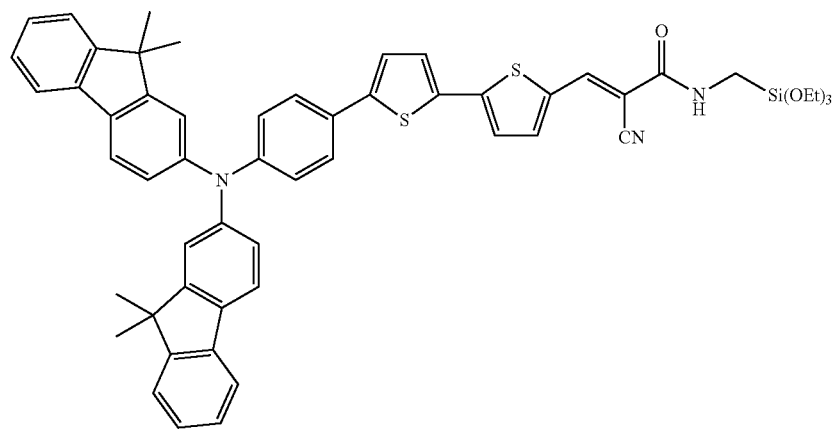

-continued
No. 57
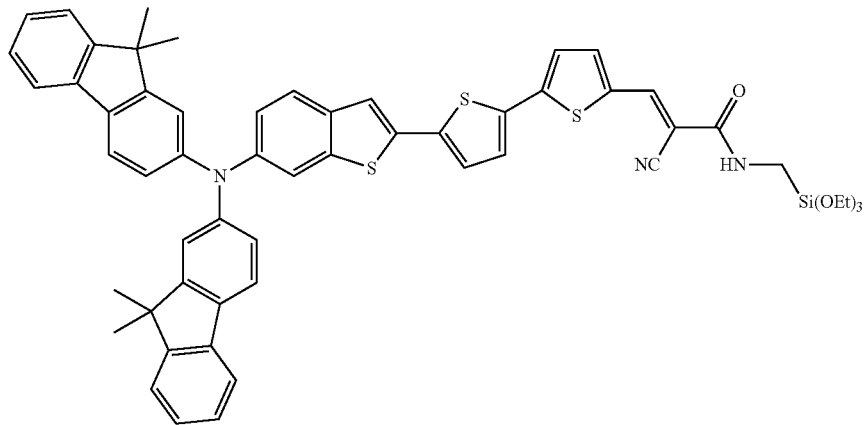
No. 58
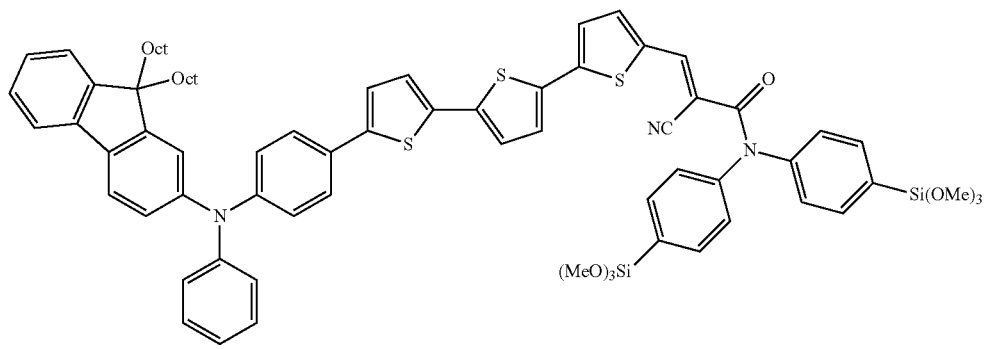
No. 59
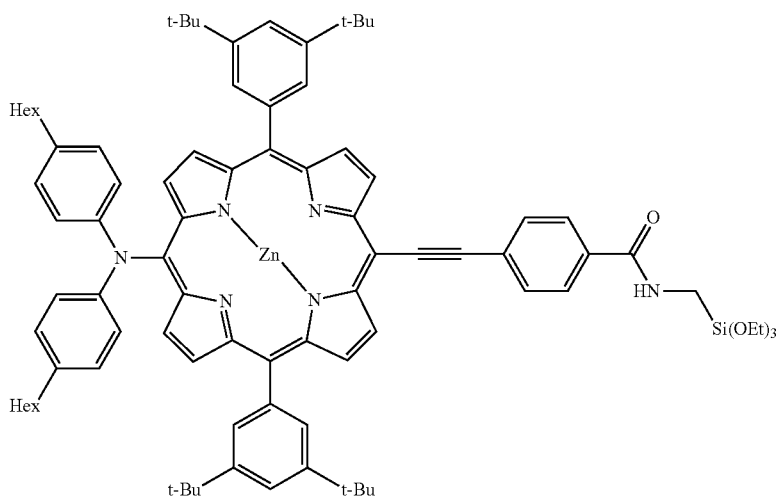

No. 60
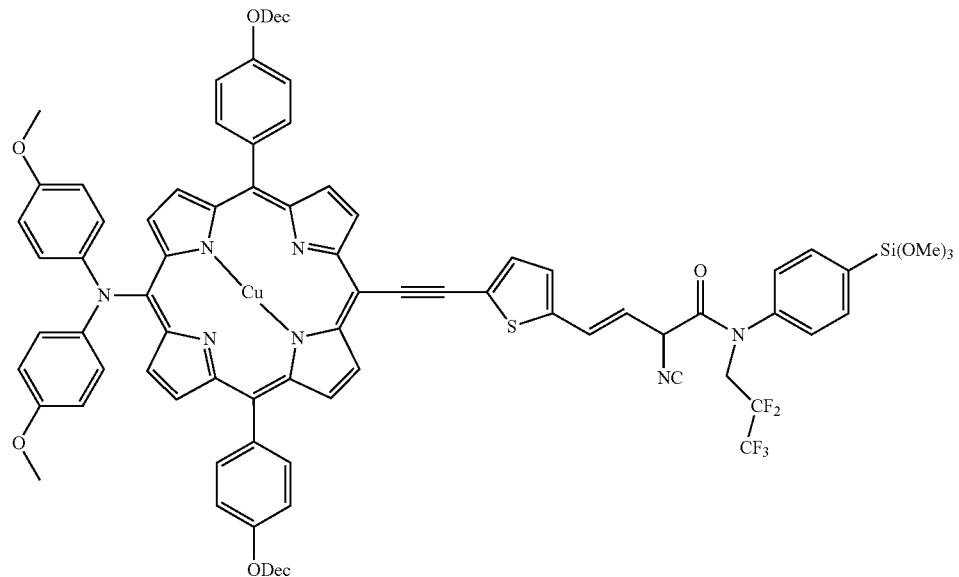
[Chemical Formula 16]
No. 61
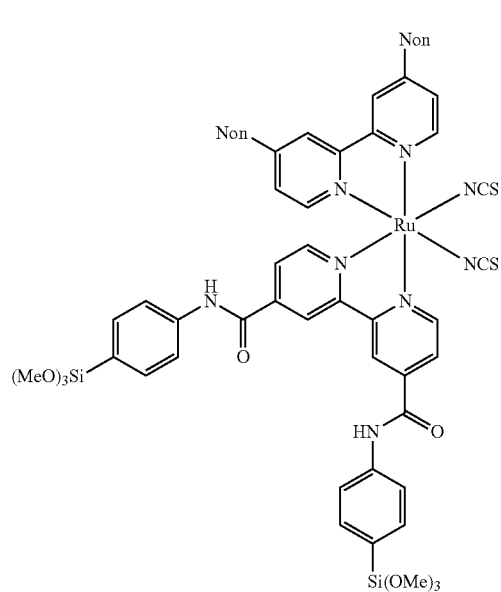
No. 62
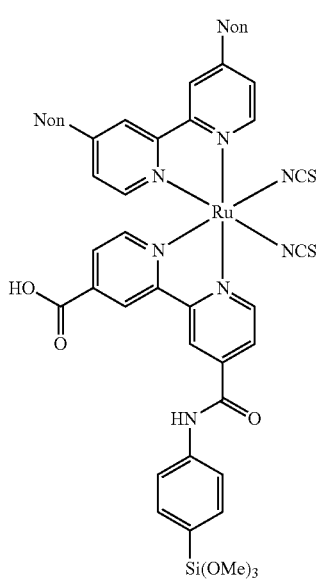

-continued
No. 63
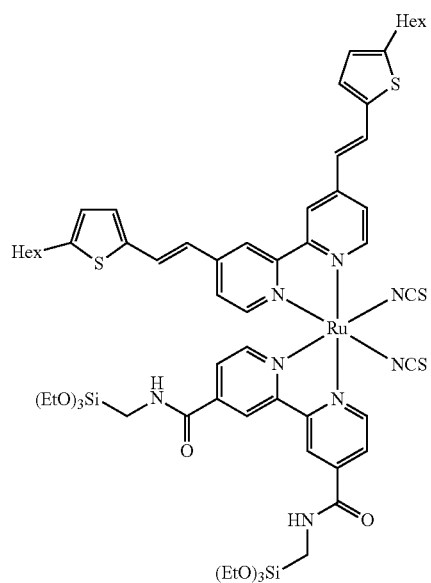
No. 64
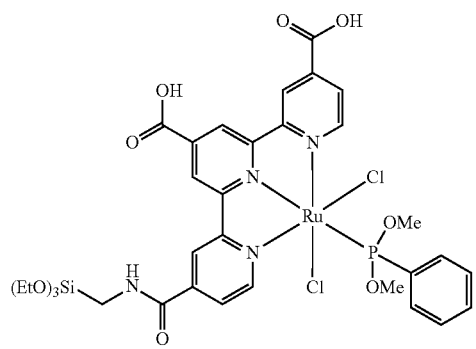
No. 65
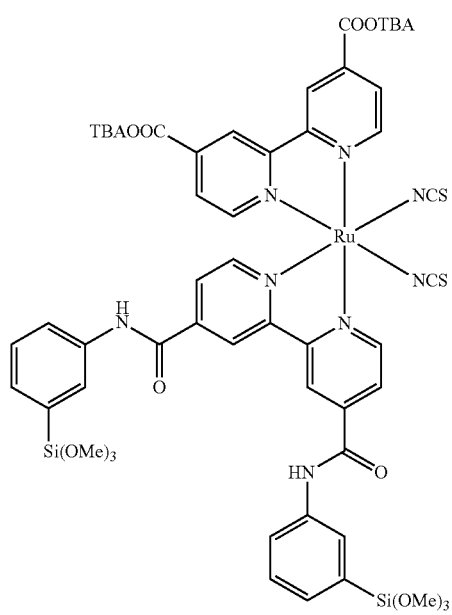
No. 66
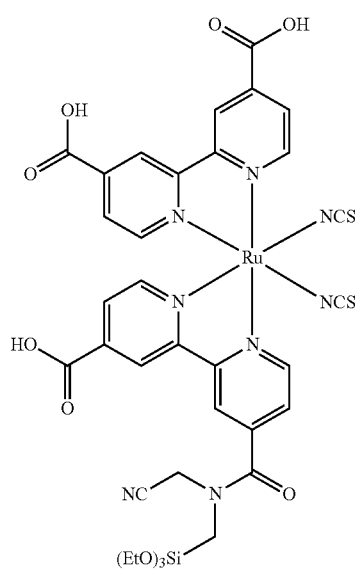

-continued
No. 67
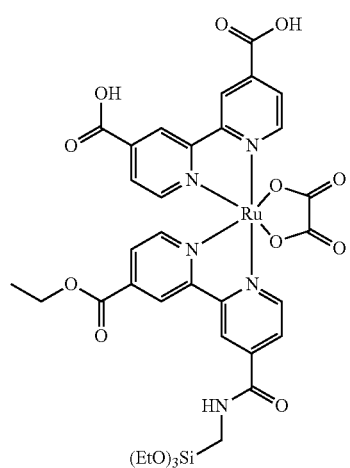
No. 68
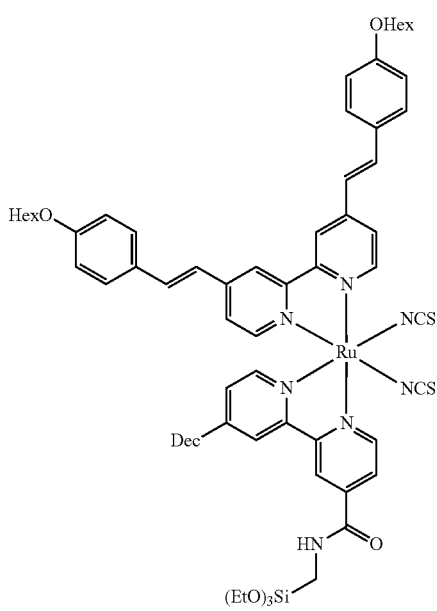
No. 69
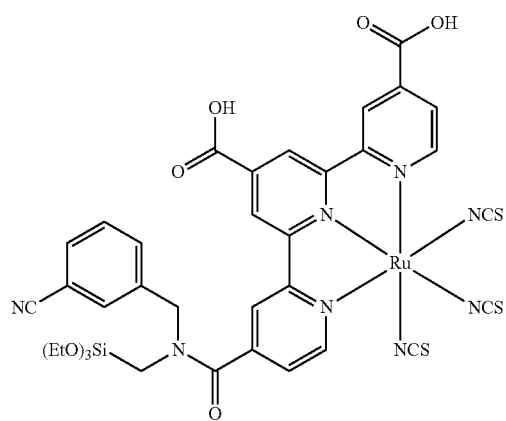
[Chemical Formula 16A]
No. 70
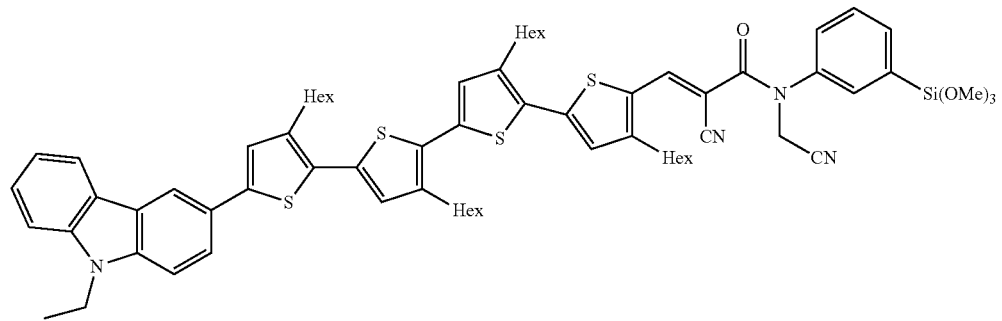

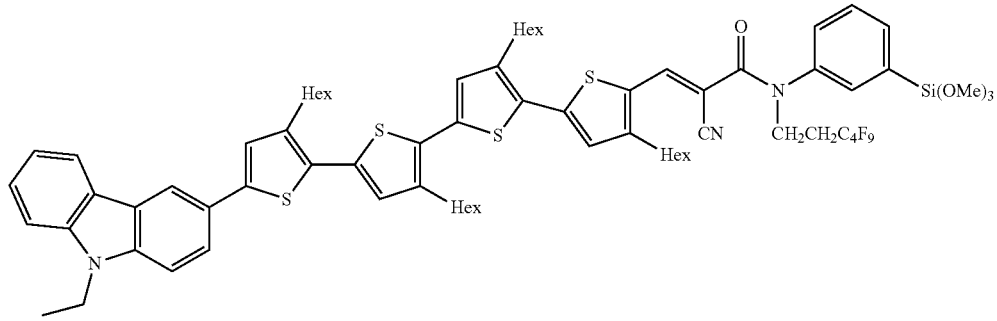

No. 71

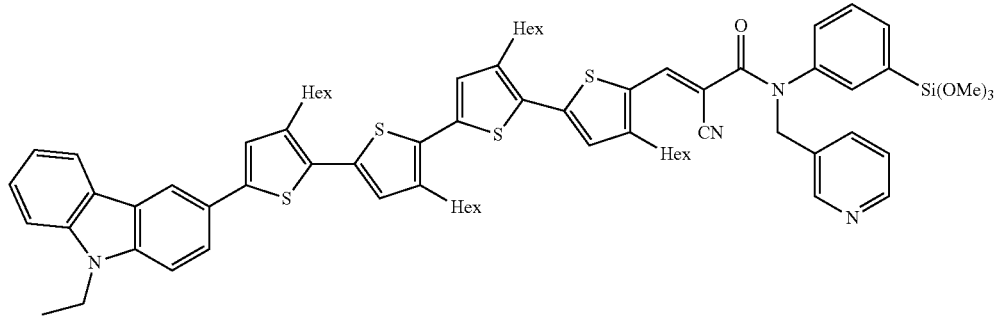

No. 72

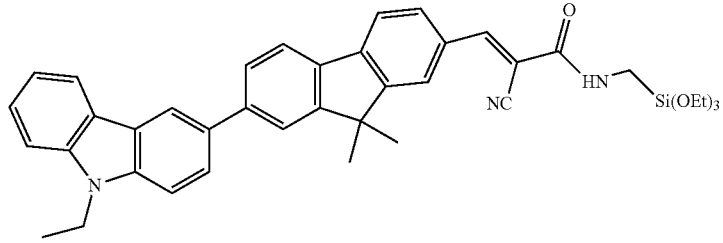

No. 73

The compound of the invention represented by formula (1) can be obtained by a method based on known or well-known general reactions, and the method for synthesizing it is not restricted. In one example of a representative synthesis method, the compound represented by formula (1) can be synthesized by converting a conjugated carboxylic acid having a carboxyl group into an acid chloride, and then making it react with a primary or secondary amine compound having a silyl group. The reagent to be used for the reaction may, as necessary, be altered, and that compound can be synthesized in a similar way when a sulfonic acid is used instead of a carboxylic acid.

The support material of the invention carrying the novel compound of the invention can be advantageously used in the photoelectric conversion device described below and also be used for catalysts, toners, and other materials.

Next, the photoelectric conversion device of the invention will be described.

The photoelectric conversion device of the invention is a dye-sensitized photoelectric conversion device, which may be the same as a conventional dye-sensitized photoelectric conversion device except that the novel compound of the invention is used therein as a dye. Hereinafter, a typical example of the structure of the photoelectric conversion device of the invention will be described with reference to FIGS. 1 and 2.

FIG. 1 schematically shows the cross-sectional structure of an example of the photoelectric conversion device of the invention. FIG. 2 extracts and shows in an enlarged manner the principal part of the photoelectric conversion device shown in FIG. 1. The photoelectric conversion device shown in FIGS. 1 and 2 corresponds to the principal part of what is called a dye-sensitized solar cell. The photoelectric conversion device has a working electrode 10 and a counter electrode 20, which are opposed to each other with an electrolyte-containing layer 30 interposed therebetween, in which at least one of the working electrode 10 and the counter electrode 20 is an optically-transparent electrode.

For example, the working electrode 10 includes a conductive substrate 11, a metal oxide semiconductor layer 12 provided on one surface (the counter electrode 20-side surface) of the substrate 11, and a dye 13 supported on the metal oxide semiconductor layer 12. In the photoelectric conversion device of the invention, the dye 13 corresponds to the novel compound of the invention represented by formula (1), and the composite of the novel compound of the invention as the dye with the metal oxide semiconductor layer 12 carrying the compound corresponds to the support material of the invention.

The working electrode 10 functions as a negative electrode for the external circuit. For example, the conductive substrate 11 comprises an insulating substrate 11A and a conductive layer 11B provided on the surface of the substrate 11A.

For example, the substrate 11A may be made of an insulating material such as glass or plastic. For example, plastic is used in the form of a transparent polymer film. Examples of plastic used to form a transparent polymer film include tetraacetyl cellulose (TAC), polyethylene terephthalate (PET), polyethylene naphthalate (PEN), syndiotactic polystyrene (SPS), polyphenylene sulfide (PPS), polycarbonate (PC), polyarylate (PAR), polysulfone (PSF), polyestersulfone (PES), polyetherimide (PEI), cyclic polyolefin, brominated phenoxy resin, etc.

Examples of the conductive layer 11B include a conductive metal oxide thin film including indium oxide, tin oxide, indium-tin complex oxide (ITO), fluorine-doped tin oxide (FTO: F—$SnO_2$), or the like; a metal thin film including gold (Au), silver (Ag), platinum (Pt), or the like; and a layer made of a metal mesh, a conductive polymer, or the like.

Alternatively, for example, the conductive substrate 11 may be a monolayer structure made of a conductive material. In this case, the conductive substrate 11 is typically made of a conductive metal oxide such as indium oxide, tin oxide, indium-tin complex oxide, or fluorine-doped tin oxide, a metal such as gold, silver, or platinum, or a conductive polymer.

The metal oxide semiconductor layer 12 is a support that carries the dye 13 thereon, and, for example, has a porous structure as shown in FIG. 2. The metal oxide semiconductor layer 12 includes a dense layer 12A and a porous layer 12B. The dense layer 12A, which is formed at the interface with the conductive substrate 11, is preferably dense and less-porous, more preferably in the form of a film. The porous layer 12B, which is formed at the surface in contact with the electrolyte-containing layer 30, preferably has a structure with a large number of pores and a large surface area, and more preferably has a porous structure made of deposited fine particles. Alternatively, for example, the metal oxide semiconductor layer 12 may be formed to have a film-shaped monolayer structure. As used herein, the term "carrying" or "supported on" refers to a state in which the dye 13 is chemically, physically, or electrically bonded or adsorbed to the porous layer 12B.

For example, the material (metal oxide semiconductor material) included in the metal oxide semiconductor layer 12 may be titanium oxide, zinc oxide, tin oxide, niobium oxide, indium oxide, zirconium oxide, tantalum oxide, vanadium oxide, yttrium oxide, aluminum oxide, or magnesium oxide. Titanium oxide and zinc oxide are particularly preferred as the metal oxide semiconductor material in that they can yield high conversion efficiency. Any of these metal oxide semiconductor materials may be used alone or in combination of two or more (as a mixture, a mixed crystal, a solid solution, a surface coating, or the like). For example, titanium oxide may be used in combination with zinc oxide or the like.

The metal oxide semiconductor layer 12 having a porous structure may be formed using a method such as an electrolytic deposition technique, a coating technique, or a firing technique. A process of forming the metal oxide semiconductor layer 12 using an electrolytic deposition technique may include providing an electrolytic bath liquid containing fine particles of a metal oxide semiconductor material and depositing the fine particles on the conductive layer 11B of the conductive substrate 11 in the electrolytic bath liquid so that the metal oxide semiconductor material is precipitated thereon. A process of forming the metal oxide semiconductor layer 12 using a coating technique may include applying, to the conductive substrate 11, a dispersion (metal oxide slurry) containing dispersed fine particles of a metal oxide semiconductor material and then drying the applied dispersion to remove the dispersion medium from the dispersion. A process of forming the metal oxide semiconductor layer 12 using a firing technique may include applying a metal oxide slurry to the conductive substrate 11 in the same way as in the coating technique, drying the slurry, and then firing the dried material. Especially when an electrolytic deposition technique or a coating technique is used to form the metal oxide semiconductor layer 12, a less heat-resistant plastic material or polymer film material can be used as the substrate 11A, so that a highly flexible electrode can be formed.

The metal oxide semiconductor layer 12 may also be treated with an organic base, a urea derivative, or a cyclic sugar chain. Examples of the organic base include diarylamine, triarylamine, pyridine, 4-tert-butylpyridine, polyvinyl pyridine, quinoline, piperidine, and amidine. The treatment may be performed before or after the dye 13 is adsorbed as described below. The treatment method may be an immersion treatment, and a solid treatment agent may be dissolved in an organic solvent and then be used for the immersion treatment.

The dye 13, which is typically adsorbed to the metal oxide semiconductor layer 12, includes one or more dyes (sensitizing dyes) capable of injecting electrons into the metal oxide semiconductor layer 12 when excited by absorbing light. In the photoelectric conversion device of the invention, the novel compound of the invention represented by formula (1) corresponds to the dye 13. When the novel compound of the invention is used as the dye 13, the ratio of the amount of electrons injected from the whole of the dye 13 into the metal oxide semiconductor layer 12 to the amount of applied light will be higher, so that the conversion efficiency will be higher.

The dye 13 only has to include at least one novel compound of the invention represented by formula (1) and may include any other dye. Examples of any other dye include organic dyes (hereinafter referred to as other organic dyes) and organometallic complex compounds, and preferably include dyes having a group capable of adsorbing to the metal oxide semiconductor layer 12 (support).

Examples of other organic dyes include eosin Y, dibromofluorescein, fluorescein, rhodamine B, pyrogallol, dichlorofluorescein, Erythrosine B (Erythrosine is a registered trademark), fluorescin, mercurochrome, cyanine dyes, merocyanine disazo dyes, trisazo dyes, anthraquinone dyes, polycyclic quinone dyes, indigo dyes, diphenylmethane dyes, trimethylmethane dyes, quinoline dyes, benzophenone dyes, naphthoquinone dyes, perylene dyes, fluorenone dyes, squarylium dyes, azulenium dyes, perinone dyes, quinacridone dyes, metal-free phthalocyanine dyes, metal-free porphyrin dyes, or metal-free azaporphyrin dyes.

Examples of organometallic complex compounds include organometallic complex compounds having both an ionic coordinate bond, which is formed between a metal cation and a nitrogen anion in an aromatic heterocyclic ring, and a nonionic coordinate bond, which is formed between a metal cation and a nitrogen atom or a chalcogen atom; and organometallic complex compounds having both an ionic coordinate bond, which is formed between a metal cation and an oxygen anion or a sulfur anion, and a nonionic coordinate bond, which is formed between a metal cation and a nitrogen atom or a chalcogen atom. Specific examples include metal phthalocyanine dyes such as copper phthalocyanine, titanyl phthalocyanine, cobalt phthalocyanine, nickel phthalocyanine, and iron phthalocyanine; metal naphthalocyanine dyes, metal porphyrin dyes, metal azaporphyrin dyes; and bipyridyl, terpyridyl, phenanthroline, bicinchoninate, azo, or quinolinol metal complexes with ruthenium, iron, or osmium, and other ruthenium complexes.

In addition to the above dye, the dye 13 may also contain one or more additives. Examples of such additives include association inhibitors capable of inhibiting the association of compounds in the dye, such as cholic acid compounds represented by formula (13) shown below. Any of such additives may be used alone or in mixture of two or more.

[Chemical Formula 17]

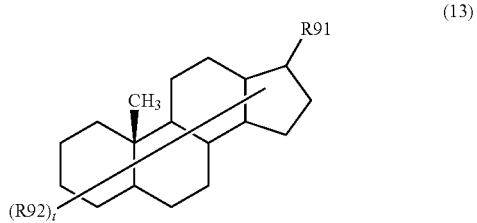

(13)

wherein R91 represents an alkyl group having an acidic group or an alkoxysilyl group, R92 represents a group bonded to any of the carbon atoms of the steroid skeleton and selected from a hydroxyl group, a halogen group, an alkyl group, an alkoxy group, an aryl group, a heterocyclic group, an acyl group, an acyloxy group, an oxycarbonyl group, an oxo group, an acidic group, an alkoxysilyl group, or a derivative of any of these groups, R92 groups may be the same or different, t represents an integer of 1 to 5, and any carbon-carbon bond in the steroid skeleton may be a single bond or a double bond.

For example, the counter electrode 20 comprises a conductive substrate 21 and a conductive layer 22 provided on the substrate 21. The counter electrode 20 functions as a positive electrode for the external circuit. Examples of the material for the conductive substrate 21 may include those for the substrate 11A of the conductive substrate 11 in the working electrode 10. The conductive layer 22 comprises one or more conductive materials and optionally a binder. For example, the conductive material used to form the conductive layer 22 may be a metal such as platinum, gold, silver, copper (Cu), rhodium (Rh), ruthenium (Ru), aluminum (Al), magnesium (Mg), or indium (In), carbon (C), or a conductive polymer. For example, the binder that may be used to form the conductive layer 22 may be acrylic resin, polyester resin, phenolic resin, epoxy resin, cellulose, melamine resin, fluoroelastomer, or polyimide resin. Alternatively, for example, the counter electrode 20 may be a monolayer structure of the conductive layer 22.

For example, the electrolyte-containing layer 30 includes a redox electrolyte having a redox couple. For example, the redox electrolyte may be an $I^-/I_3^-$ system, a $Br^-/Br_3^-$ system, a quinone/hydroquinone system, a Co complex system, or a nitroxy radical compound system. More specifically, the redox electrolyte may be a combination of a halide salt and elementary halogen, such as a combination of an iodide salt and elementary iodine or a combination of a bromide salt and elementary bromine Examples of such a halide salt include cesium halide, quaternary alkyl ammonium halides, imidazolium halides, thiazolium halides, oxazolium halides, quinolinium halides, or pyridinium halides. Specific examples of the iodide salts include cesium iodide, quaternary alkyl ammonium iodides such as tetraethyl ammonium iodide, tetrapropyl ammonium iodide, tetrabutyl ammonium iodide, tetrapentyl ammonium iodide, tetrahexyl ammonium iodide, tetraheptyl ammonium iodide, or trimethylphenyl ammonium iodide; imidazolium iodides such as 3-methylimidazolium iodide or 1-propyl-2,3-dimethylimidazolium iodide; thiazolium iodides such as 3-ethyl-2-methyl-2-thiazolium iodide, 3-ethyl-5-(2-hydroxyethyl)-4-methylthiazolium iodide, or 3-ethyl-2-methylbenzothiazolium iodide; oxazolium iodides such as 3-ethyl-2-methyl-benzoxazolium iodide; quinolinium iodides such as 1-ethyl-2-methylquinolinium iodide; and pyridinium iodides. Examples of the bromide salts include quaternary alkyl ammonium bromide. The combination of a halide salt and elementary halogen is preferably a combination of at least one of the above iodide salts and elementary iodine.

Alternatively, for example, the redox electrolyte may a combination of an ionic liquid and elementary halogen. In this case, the redox electrolyte may further contain the halide salt or the like. Examples of the ionic liquid include those capable of being used in batteries or solar cells, such as those disclosed in publications for example Inorg. Chem. (1996), 35, pp. 1168-1178, Electrochemistry (2002), 2, pp. 130-136, Japanese Patent Application National Publication (Laid-Open) No. 09-507334, or JP 08-259543 A. In particular, the ionic liquid is preferably a salt having a melting point lower than room temperature (25° C.) or a salt that can be liquefied at room temperature when dissolved with any other molten salt or the like although it has a melting point higher than room temperature. Examples of the ionic liquid include the anions and the cations shown below.

Examples of ionic liquid cations include ammonium, imidazolium, oxazolium, thiazolium, oxadiazolium, triazolium, pyrrolidinium, pyridinium, piperidinium, pyrazolium, pyrimidinium, pyrazinium, triazinium, phosphonium, sulfonium, carbazolium, indolium, or a derivative of any of the above. Any of these cations may be used alone or in mixture of two or more. Specific examples include 1-methyl-3-propylimidazolium, 1-butyl-3-methylimidazolium, 1,2-dimethyl-3-propylimidazolium, and 1-ethyl-3-methylimidazolium.

Examples of ionic liquid anions include metal chlorides such as $AlCl_4^-$ and $Al_2Cl_7^-$, fluorine-containing ions such as $PF_6^-$, $BF_4^-$, $CF_3SO_3^-$, $N(CF_3SO_2)_2^-$, $F(HF)_n^-$, and $CF_3COO^-$, fluorine-free compound ions such as $NO_3^-$, $CH_3COO^-$, $C_6H_{11}COO^-$, $CH_3OSO_3^-$, $CH_3OSO_2^-$, $CH_3SO_3^-$, $CH_3SO_2^-$, $(CH_3O)_2PO_2^-$, $N(CN)_2^-$, and $SCN^-$ and halide ions such as iodide ions, and bromide ions. Any of these cations may be used alone or in mixture of two or more. In particular, the ionic liquid anion is preferably an iodide ion.

The electrolyte-containing layer 30 may comprise a liquid electrolyte (electrolytic solution), which is a solution of the redox electrolyte in a solvent, or may comprise a solid polymer electrolyte having a polymer material and an electrolytic solution held in the polymer material. Alternatively, the electrolyte-containing layer 30 may be a solidified (paste-like) electrolyte including a mixture of an electrolytic solution and a particulate carbon material such as carbon black. The carbon material-containing solidified electrolyte does not need to contain elementary halogen because the carbon material has the function of catalyzing the redox reaction. The redox electrolyte may contain one or more organic solvents in which the halide salt, the ionic liquid, or the like is soluble. The organic solvent may be an electrochemically inert organic solvent, such as acetonitrile, tetrahydrofuran, propionitrile, butyronitrile, methoxyacetonitrile, 3-methoxypropionitrile, valeronitrile, dimethyl carbonate, ethyl methyl carbonate, ethylene carbonate, propylene carbonate, N-methylpyrrolidone, pentanol, quinoline, N,N-dimethylformamide, γ-butyrolactone, dimethyl sulfoxide, or 1,4-dioxane.

For improving the photoelectric conversion device in generating efficiency, durability, etc., the electrolyte-containing layer 30 may also contain an additive such as an acyclic sugar (JP 2005-093313 A), a pyridine compound (JP 2003-331936 A), a urea derivative (JP 2003-168493 A), etc.

When the dye 13 supported on the working electrode 10 in the photoelectric conversion device is irradiated with light (sunlight, or ultraviolet light, visible light, or near infrared light equivalent to sunlight), the dye 13 is excited by absorbing the light to inject electrons into the metal oxide semiconductor layer 12. The electrons are transferred to the adjacent conductive layer 11B and then reach the counter electrode 20 via the external circuit. On the other hand, in the electrolyte-containing layer 30, the electrolyte is oxidized so that the dye 13 which has been oxidized with the electron transfer can return (or be reduced) to its ground state. The oxidized electrolyte is reduced by receiving electrons that have reached the counter electrode 20. Thus, the electrons transfer between the working electrode 10 and the counter electrode 20 and the associated redox reaction in the electrolyte-containing layer 30 are repeated. This generates continuous transfer of electrons to enable steady photoelectric conversion.

For example, the photoelectric conversion device of the invention can be fabricated as described below.

The working electrode 10 is first formed. The metal oxide semiconductor layer 12 having a porous structure is first formed on the conductive layer 11B-side surface of the conductive substrate 11 using an electrolytic deposition technique or a firing technique. When the metal oxide semiconductor layer 12 is formed using an electrolytic deposition technique, for example, an electrolyte bath containing a metal salt for forming a metal oxide semiconductor material is set to a predetermined temperature while the electrolyte bath is bubbled with oxygen or air, and the conductive substrate 11 is immersed in the electrolyte bath when a constant voltage is applied between the conductive substrate 11 and a counter electrode. In this process, the metal oxide semiconductor material is deposited on the conductive layer 11B so as to form a porous structure. In this process, the counter electrode may be shifted as needed in the electrolyte bath. When the metal oxide semiconductor layer 12 is formed using a firing technique, for example, a metal oxide slurry, which is prepared by dispersing a powder of a metal oxide semiconductor material in a dispersion medium, is applied to the conductive substrate 11, dried, and then fired to form a porous structure. Subsequently, the dye 13 including the novel compound of the invention represented by formula (1) is dissolved in an organic solvent to form a dye solution. The conductive substrate 11 with the metal oxide semiconductor layer 12 formed thereon is immersed in the dye solution so that the dye 13 is deposited (supported) on the metal oxide semiconductor layer 12.

The concentration of the novel compound of the invention in the dye solution is preferably from $1.0 \times 10^{-5}$ to $1.0 \times 10^{-3}$ mol/dm$^3$, more preferably $5.0 \times 10^{-5}$ to $5.0 \times 10^{-4}$ mol/dm$^3$. The solvent used to form the dye solution may be of any type capable of dissolving the novel compound of the invention, examples of which include hydrocarbons such as toluene, benzene, and xylene; alcohols such as methanol, ethanol, and tert-butanol; ether alcohols such as methyl cellosolve, ethyl cellosolve, butyl cellosolve, and butyl diglycol; ketones such as acetone, methyl ethyl ketone, methyl isobutyl ketone, cyclohexanone, and diacetone alcohol; esters such as ethyl acetate, butyl acetate, and methoxyethyl acetate; acrylic esters such as ethyl acrylate and butyl acrylate; fluorinated alcohols such as 2,2,3,3,-tetrafluoropropanol; chlorinated hydrocarbons such as methylene dichloride, dichloroethane, and chloroform; acetonitrile and tetrahydrofuran. Any of these organic solvents may be mixed together as desired. Toluene and acetonitrile are preferred.

Subsequently, the conductive layer 22 is formed on one side of the conductive substrate 21 to form the counter electrode 20. For example, the conductive layer 22 is formed by sputtering of a conductive material.

Finally, the dye 13-carrying surface of the working electrode 10 and the conductive layer 22-side surface of the counter electrode 20 are opposed to each other with a predetermined distance kept therebetween, and are fixed with a spacer (not shown) such as a sealant. And then, the whole is sealed, for example, except for the inlet for the electrolyte. Subsequently, the electrolyte is injected between the working electrode 10 and the counter electrode 20, and then the inlet is sealed, so that the electrolyte-containing layer 30 is formed. Thus, the photoelectric conversion device shown in FIGS. 1 and 2 is completed.

In the photoelectric conversion device of the invention, the dye 13 includes the compound of the invention represented by formula (1), and thus the dye 13 is prevented from leaching into the electrolyte-containing layer 30 from the support material (metal oxide semiconductor layer 12) carrying the dye 13, in contrast to cases where compounds other than the compound of the invention are used. Thus, the amount of the dye 13 supported on the metal oxide semiconductor layer 12 will not decrease, so that the amount of electrons injected from the dye 13 into the metal oxide semiconductor layer 12 will not decrease. Because of such an effect, the photoelectric conversion device of the invention can have higher durability.

Although the photoelectric conversion device described above has the electrolyte-containing layer 30 between the working electrode 10 and the counter electrode 20, the electrolyte-containing layer 30 may be replaced by a solid charge-transfer layer. In this case, for example, the solid charge-transfer layer has a solid material in which carrier transport takes part in electrical conduction. Such a material is preferably an electron transport material, a hole transport material, or the like.

The hole transport material is preferably an aromatic amine or a triphenylene derivative. Examples of the hole transport material include organic conductive polymers such as oligothiophene compounds, polypyrrole, polyacetylene or derivatives thereof, poly(p-phenylene) or derivatives thereof, poly(p-phenylenevinylene) or derivatives thereof, polythienylene vinylene or derivatives thereof, polythiophene or derivatives thereof, polyaniline or derivatives thereof, and polytoluidine or derivatives thereof.

Alternatively, for example, a p-type inorganic compound semiconductor may be used as the hole transport material. The p-type inorganic compound semiconductor is preferably has a band gap of 2 eV or more, more preferably 2.5 eV or more. The p-type inorganic compound semiconductor must have an ionization potential smaller than that of the working electrode 10 to allow the dye with holes to be reduced. Although the preferred range of the ionization potential of the p-type inorganic compound semiconductor varies with the dye used, the ionization potential is preferably in the range of 4.5 eV to 5.5 eV, more preferably in the range of 4.7 eV to 5.3 eV.

For example, the p-type inorganic compound semiconductor may be a monovalent copper compound semiconductor. Examples of the monovalent copper compound semiconductor include CuI, CuSCN, CuInSe$_2$, Cu(In,Ga)Se$_2$, CuGaSe$_2$, Cu$_2$O, CuS, CuGaS$_2$, CuInS$_2$, CuAlSe$_2$, etc. Other examples of the p-type inorganic compound semiconductor include GaP, NiO, CoO, FeO, Bi$_2$O$_3$, MoO$_2$, Cr$_2$O$_3$, etc.

For example, such a solid charge-transfer layer may be formed by a method of forming a solid charge-transfer layer directly on the working electrode 10, which may be followed by forming the counter electrode 20.

For example, the hole transport material including an organic conductive polymer can be introduced into the interior of the electrode by a technique such as vacuum deposition, casting, coating, spin coating, immersion, electrolytic polymerization, or photo-electrolytic polymerization. The solid inorganic compound can also be introduced into the interior of the electrode by a technique such as casting, coating, spin coating, immersion, or electroplating. Part of the solid charge-transfer layer formed as described above (especially having a hole transport material) is preferably infiltrated into part of the pores of the porous structure of the metal oxide semiconductor layer 12 so that it can be in direct contact with dye 13.

As in the case that the electrolyte-containing layer 30 is provided, the compound of the invention can also increase the conversion efficiency of the photoelectric conversion device having the solid charge-transfer layer in place of the electrolyte-containing layer 30.

The photoelectric conversion device of the invention may be used not only in solar cell applications as described above but also in other applications. For example, other applications include optical sensors, etc.

As described above, the novel compound of the invention may be supported on a support, and such a support material carrying the novel compound of the invention is advantageously used in applications such as photoelectric conversion devices. The novel compound of the invention can also be used in other applications such as synthetic intermediates for optical recording materials, pharmaceuticals, agricultural chemicals, perfumes, dyes, etc.; a variety of functional materials and raw materials for polymers; photoelectrochemical cells, non-linear optical devices, electrochromic displays, holograms, organic semiconductors, and organic ELs; silver halide photographic materials, photosensitizers; colorants for use in printing ink, inkjet printing, electrophotographic color toners, cosmetics, and plastics; protein staining agents and luminescent dyes for use in detection of substances; and raw materials for synthetic quartz, paints, synthetic catalysts, catalyst supports, surface coating thin film materials, silicone rubber crosslinking agents, and thickening and binding agents.

EXAMPLES

Hereinafter, the invention is more specifically described with reference to synthesis examples of the novel compound of the invention, examples of support materials (working electrodes) using the compounds synthesized in the synthesis examples, and comparative examples. However, these examples are not intended to limit the invention.

The synthesis examples below show the synthesis of compound Nos. 1 to 24, 61, 62, and 70 to 72 listed above. Carboxylic acid forms and amine compounds as precursors were purchased or synthesized by known methods.

Synthesis Example 1

Synthesis of Compound No. 1

MK-2-Dye (available from Sigma Aldrich, 0.10 mmol, 96 mg), oxalyl chloride (0.11 mmol, 14 mg), dimethylformamide (0.01 ml), and chloroform (2 ml) were charged into a flask and then stirred at 25° C. for 1 hour to obtain a reaction solution. After cooling to 10° C., N,N-diisopropylethylamine (0.20 mmol, 26 mg) and (triethoxysilylmethyl)hexylamine (0.10 mmol, 28 mg) were added and further stirred for 1 hour. Water (2 ml) was added to the reaction solution, and oil-water separation was performed. The resultant organic layer was purified using silica gel column chromatography (mobile phase; chloroform) to yield 108 mg (yield 89%) of a purple solid. The resultant solid was identified as compound No. 1 using UV-VIS (λmax) and $^1$H-NMR. The data are shown in Tables 1 and 2-1.

Synthesis Examples 2 to 29

Compound Nos. 2 to 24, 61, 62, and 70 to 72

Compound Nos. 2 to 24, 61, 62, and 70 to 72 were synthesized using the same method as in Synthesis Example 1, except that compounds with a carboxyl group or a sulfo group and amine compounds corresponded to the desired compounds were used instead. The appearance and yield of each resultant compound are shown in Table 1. The synthesized compounds were each identified as the desired compound in the same way as in Synthesis Example 1. The data are shown in Tables 1, 2-1, 2-2, and 2-3.

TABLE 1

| | Compound | Appearance | Yield/% | λ max/nm |
|---|---|---|---|---|
| Synthesis Example 1 | No. 1 | Violet solid | 89 | 473 (CHCl$_3$) |
| Synthesis Example 2 | No. 2 | Violet solid | 86 | 475 (CHCl$_3$) |
| Synthesis Example 3 | No. 3 | Violet solid | 69 | 506 (CHCl$_3$) |
| Synthesis Example 4 | No. 4 | Violet solid | 89 | 492 (CHCl$_3$) |
| Synthesis Example 5 | No. 5 | Violet solid | 59 | 492 (CHCl$_3$) |
| Synthesis Example 6 | No. 6 | Violet solid | 25 | 480 (CHCl$_3$) |
| Synthesis Example 7 | No. 7 | Violet solid | 82 | 504 (CHCl$_3$) |
| Synthesis Example 8 | No. 8 | Violet solid | 74 | 505 (CHCl$_3$) |
| Synthesis Example 9 | No. 9 | Yellow solid | 30 | 381 (MeOH) |
| Synthesis Example 10 | No. 10 | Deep green solid | 17 | 499 (CHCl$_3$) |
| Synthesis Example 11 | No. 11 | Deep green solid | 39 | 511 (CHCl$_3$) |
| Synthesis Example 12 | No. 12 | Red solid | 28 | 484 (CHCl$_3$) |
| Synthesis Example 13 | No. 13 | Red solid | 40 | 509 (CHCl$_3$) |
| Synthesis Example 14 | No. 14 | Orange solid | 34 | 443 (CHCl$_3$) |
| Synthesis Example 15 | No. 15 | Deep blue solid | 31 | 641 (CHCl$_3$) |
| Synthesis Example 16 | No. 16 | Burgundy solid | 57 | 554 (CHCl$_3$) |
| Synthesis Example 17 | No. 17 | Green solid | 13 | 568 (CHCl$_3$) |
| Synthesis Example 18 | No. 18 | Brown solid | 76 | 435 (MeOH) |
| Synthesis Example 19 | No. 19 | Orange solid | 8 | 423 (MeOH) |
| Synthesis Example 20 | No. 20 | Orange solid | 15 | 426 (MeOH) |
| Synthesis Example 21 | No. 21 | Violet solid | 81 | 419 (CHCl$_3$) |
| Synthesis Example 22 | No. 22 | Violet solid | 77 | 423 (CHCl$_3$) |
| Synthesis Example 23 | No. 23 | Violet solid | 96 | 497 (CHCl$_3$) |
| Synthesis Example 24 | No. 24 | Deep green solid | 79 | 516 (CHCl$_3$) |
| Synthesis Example 25 | No. 61 | Violet solid | 55 | 418 (CHCl$_3$) |
| Synthesis Example 26 | No. 62 | Violet solid | 78 | 418 (CHCl$_3$) |
| Synthesis Example 27 | No. 70 | Violet solid | 44 | 503 (CHCl$_3$) |
| Synthesis Example 28 | No. 71 | Violet solid | 70 | 490 (CHCl$_3$) |
| Synthesis Example 29 | No. 72 | Violet solid | 52 | 489 (CHCl$_3$) |

TABLE 2-1

<sup>1</sup>H-NMR; CDCl₃

| Compound | ¹H NMR |
|---|---|
| No. 1 | 8.30 (s, 1H), 8.13 (d, 1H), 7.97 (s, 1H), 7.72 (d, 1H), 7.48 (t, 1H), 7.41 (t, 2H), 7.25 (s, 1H), 7.19 (s, 1H), 7.03-7.00 (m, 3H), 4.38 (q, 2H), 3.90 (q, 6H), 3.59 (t, 2H), 3.06 (br s, 2H), 2.87-2.71 (m, 8H), 1.77-1.23 (m, 52H), 0.93-0.88 (m, 15H) |
| No. 2 | 8.51 (s, 1H), 8.30 (s, 1H), 8.13 (d, 1H), 7.99 (s, 1H), 7.71 (d, 1H), 7.48 (t, 1H), 7.41 (t, 2H), 7.25 (s, 1H), 7.19 (s, 1H), 7.06-7.00 (m, 3H), 6.88 (t, 2H), 4.95 (s, 2H), 4.39 (q, 2H), 3.87 (q, 6H), 2.96-2.73 (m, 10H), 1.71-1.34 (m, 35H), 1.24 (t, 9H), 0.92-0.89 (m, 12H) |
| No. 3 | 8.55 (s, 1H), 8.30 (s, 1H), 8.13 (d, 1H), 7.71 (d, 1H), 7.48 (t, 1H), 7.41 (t, 3H), 7.27-7.19 (m, 3H), 7.11-6.97 (m, 4H), 4.38 (q, 2H), 4.31 (q, 6H), 2.84-2.75 (m, 8H), 1.74-1.24 (m, 35H), 1.20 (t, 9H), 0.92-0.88 (m, 12H) |
| No. 4 | 8.46 (s, 1H), 8 31 (s, 1H), 8.14 (d, 1H), 7.72 (d, 1H), 7.49 (t, 1H), 7.41 (t, 2H), 7.27-7.19 (m, 2H), 7.06-7.01 (m, 3H), 6.37 (t, 1H), 4.39 (q, 2H), 3.90 (q, 6H), 2.97 (d, 2H), 2.88-2.82 (m, 8H), 1.75-1.23 (m, 44H), 0.92-0.89 (m, 12H) |
| No. 5 | 8.40 (s, 1H), 8.30 (s, 1H), 8.14 (d, 1H), 7.72 (d, 1H), 7.49 (t, 1H), 7.41 (t, 2H), 7.25 (s, 1H), 7.19 (s, 1H), 7.09-7.00 (m, 3H), 4.70 (s, 2H), 4.39 (q, 2H), 4.22 (s, 2H), 4.31 (q, 6H), 2.89-2.76 (m, 8H), 1.72-1.24 (m, 44H), 0.92-0.88 (m, 8H) |
| No. 6 | 8.30 (s 1H), 8.14 (d, 1H), 8.09 (s, 1H), 7.72 (d, 1H), 7.49 (t, 1H), 7.41 (t, 2H), 7.26 (s, 1H), 7.19 (s, 1H), 7.05 (s, 1H), 7.01 (d, 2H), 5.47 (br s, 2H), 4.39 (q, 2H), 4.27 (s, 2H), 3.91 (q, 6H), 3.13 (s, 2H), 2.88-2.73 (m, 8H), 1.79-1.31 (m, 35H), 1.25 (t, 9H), 0.93-0.88 (m, 12H) |
| No. 7 | 8.31 (s, 1H), 8.14 (d, 1H), 7.96 (s, 1H), 7.73-7.67 (m, 5H), 7.49 (t, 1H), 7.41 (t, 2H), 7.26 (s, 1H), 7.20 (s, 1H), 7.10 (s, 1H), 7.02 (s, 2H), 4.39 (q, 2H), 3.63 (s, 9H), 2.90-2.81 (m, 8H), 1.76-1.35 (m, 35H), 0.93-0.88 (m, 12H) |
| No. 8 | 8.59 (s, 1H), 8 31 (s, 1H), 8.14 (d, 1H), 7.94 (s, 1H), 7.88 (dt, 1H), 7.73 (s, 1H), 7.71 (s, 1H), 7.51-7.39 (m, 5H), 7.25 (s, 1H), 7.20 (s, 1H), 7.10 (s, 1H), 7.02 (s, 2H), 4.39 (q, 2H), 3.65 (s, 9H), 2.90-2.81 (m, 8H), 1.79-1.32 (m, 35H), 0.94-0.88 (m, 12H) |
| No. 9 | 8.18 (d, 1H), 8.13 (d, 1H), 7.98 (s, 1H), 7.94 (s, 1H), 7.81 (d, 1H), 7.70 (d, 1H), 7.54 (m, 2H), 7.29 (d, 2H), 7.18 (d, 2H), 4.49 (q, 2H), 3.45 (s, 9H), 1.34 (t, 3H) |
| No. 10 | 7.89-7.85 (m, 2H), 7.56-7.52 (m, 2H), 7.35-7.29 (m, 1H), 7.17-7.14 (m, 2H), 3.93 (q, 6H), 3.57 (t, 2H), 3.33 (t, 2H), 3.25 (t, 2H), 3.04 (s, 2H), 1.84-1.75 (m, 6H), 1.56 (s, 6H), 1.37-1.17 (m, 21H), 0.88 (t, 3H) |
| No. 11 | 8.31 (s, 1H), 7.89 (s, 1H), 7.58 (dd, 2H), 7.35 (d, 1H), 7.26 (s, 1H), 7.16 (s, 1H), 6.34 (s, 1H), 3.89 (q, 6H), 3.34 (t, 2H), 3.26 (t, 2H), 2.96 (d, 2H), 1.82 (t, 2H), 1.77 (t, 2H), 1.58 (s, 6H), 1.32-1.23 (m, 15H) |
| No. 12 | 8.32 (s, 1H), 8.00 (s, 1H), 7.79 (d, 1H), 7.73 (d, 1H), 7.36 (d, 1H), 6.63 (dd, 1H), 6.51 (d, 1H), 6.36 (s, 1H), 3.90 (q, 6H), 3.45 (q, 4H), 2.96 (s, 2H), 1.24 (m, 15H) |

TABLE 2-2

<sup>1</sup>H-NMR; CDCl₃

| Compound | ¹H NMR |
|---|---|
| No. 13 | 8.45 (s, 1H), 8.06 (s, 1H), 7.93 (s, 1H), 7.82 (d, 2H), 7.67 (m, 4H), 7.39 (d, 1H), 6.65 (dd, 1H), 6.53 (d, 1H), 3.62 (s, 9H), 3.46 (q, 4H), 1.25 (t, 6H) |
| No. 14 | 7.87-7.80 (m, 5H), 7.52 (d, 2H), 7.43 (d, 2H), 7.11 (d, 2H), 6.74 (d, 2H), 3.60 (s, 9H), 3.11 (s, 6H) |
| No. 15 | 8.04 (d, 1H), 7.97 (s, 1H), 7.39 (m, 1H), 7.33 (d, 1H), 7.21 (dd, 1H), 7.06 (d, 1H), 6.94 (dd, 1H), 6.06 (s, 1H), 6.01 (s, 1H), 4.39 (q, 2H), 4.15 (m, 2H), 3.95 (m, 2H), 3.85 (q, 6H), 1.81 (s, 6H), 1.80 (s, 6H), 1.44 (m, 12H), 1.22 (m, 12H), 0.86 (t, 3H) |
| No. 16 | 7.73 (s, 1H), 7.62-7.56 (m, 3H), 7.41-7.25 (m, 13H), 7.07-7.01 (m, 4H), 6.95 (s, 1H), 6.93 (d, 1H), 4.91 (s, 2H), 4.06 (t, 2H), 3.60 (s, 9H), 2.17-1.25 (m, 18H), 0.88 (t, 3H) |
| No. 17 | 8.27 (d, 1H), 8.21 (d, 1H), 7.88 (d, 1H), 7.76 (d, 1H), 7.62 (t, 1H), 7.41 (t, 1H), 6.92-6.77 (m, 4H), 6.44 (t, 1H), 6.38 (d, 1H), 5.80 (t, 1H), 5.41 (d, 1H), 4.77 (d, 2H), 4.19 (q, 2H), 3.86 (q, 6H), 3.51 (d, 2H), 3.06 (s, 3H), 2.89 (d, 2H), 2.15 (s, 3H), 1.30 (t, 3H), 1.24 (t, 9H) |
| No. 18 | 7.63 (d, 1H), 7.42 (d, 1H), 7.29 (m, 4H), 7.10 (m, 3H), 6.90 (m, 1H), 6.69 (m, 1H), 3.62 (s, 3H), 3.59 (s, 3H), 3.45 (s, 9H), 3.37 (m, 3H) |
| No. 19 | 8.26 (s, 1H), 7.98 (s, 1H), 7.83 (m, 2H), 7.66 (m, 4H), 7.35 (m, 4H), 7.18 (m, 6H), 7.00 (d, 2H), 3.62 (s, 9H) |
| No. 20 | 8.20 (s, 1H), 7.89 (m, 2H), 7.65 (m, 1H), 7.49 (d, 1H), 7.16 (d, 1H), 6.66 (m, 3H), 3.62 (s, 9H), 3.43 (q, 4H), 1.22 (t, 6H) |
| No. 21 | 8.87-8.85 (m, 6H), 8.79 (d, 2H), 8.35 (d, 2H), 8.26 (d, 2H), 8.21-8.18 (m, 6H), 7.86 (d, 2H), 7.78-7.74 (m, 11H), 3.67 (s, 9H), −2.77 (s, 2H) |
| No. 22 | 8.98-8.95 (m, 6H), 8.90 (d, 2H), 8.36 (d, 2H), 8.25 (d, 2H), 8.22-8.18 (m, 6H), 7.85 (d, 2H), 7.77-7.75 (m, 11H), 3.68 (s, 9H) |

TABLE 2-2-continued

<¹H-NMR; CDCl₃>

| Compound | ¹H NMR |
|---|---|
| No. 23 | 8.48 (s, 1H), 8.30 (s, 1H), 8.14 (d, 1H), 7.72 (d, 1H), 7.47 (t, 1H), 7.41 (t, 2H), 7.25 (s, 1H), 7.19 (s, 1H), 7.06 (s, 1H), 7.01 (d, 2H), 6.46 (t, 1H), 4.39 (q, 2H), 3.84 (q, 6H), 3.43 (q, 2H), 2.88-2.79 (m, 8H), 1.77-1.63 (m, 10H), 1.36 (t, 3H), 1.34-1.31 (m, 24H), 1.25 (t, 9H), 0.94-0.89 (m, 12H), 0.69 (t, 2H) |
| No. 24 | 8.32 (s, 1H), 7.89 (s, 1H), 7.59 (d, 1H), 7.56 (d, 1H), 7.35 (d, 1H), 7.26 (d, 1H), 7.16 (s, 1H), 6.45 (t, 1H), 3.85 (q, 6H), 3.44 (q, 2H), 3.34 (t, 2H), 3.26 (t, 2H), 1.84-1.69 (m, 6H), 1.58 (s, 6H), 1.32 (s, 6H), 1.23 (t, 9H), 0.68 (t, 2H) |

TABLE 2-3

<¹H-NMR; CDCl₃>

| Compound | ¹H NMR |
|---|---|
| No. 61 | 9.43 (d, 1H), 9.32 (d, 1H), 8.22-6.70 (m, 22H), 3.60 (s, 18H), 2.89 (t, 4H), 2.57 (quin, 4H), 1.84-1.23 (m, 24H), 0.90-0.86 (m, 6H) |
| No. 62 | 9.52 (d, 1H), 9.39 (d, 1H), 8.01-6.73 (m, 17H), 3.64 (s, 9H), 2.88 (t, 4H), 2.59 (quin, 4H), 1.82-1.23 (m, 24H), 0.90-0.86 (m, 6H) |
| No. 70 | 8.45 (s, 1H), 8.30 (d, 1H), 8.13 (d, 1H), 7.75 (d, 1H), 7.71 (dd, 1H), 7.59-7.39 (m, 6H), 7.25 (s, 1H), 7.19 (s, 1H), 7.06 (s, 1H), 7.00 (s, 1H), 6.97 (s, 1H), 4.67 (s, 2H), 4.38 (q, 2H), 3.60 (s, 9H), 2.84-2.74 (m, 8H), 1.76-1.59 (m, 8H), 1.48-1.27 (m, 27H), 0.94-0.85 (m, 12H) |
| No. 71 | 8.34 (s, 1H), 8.30 (s, 1H), 8.13 (d, 1H), 7.72-7.70 (m, 2H), 7.55-7.39 (m, 5H), 7.34 (d, 1H), 7.25 (s, 1H), 7.19 (s, 1H), 7.03 (s, 1H), 7.00 (s, 1H), 6.96 (s, 1H), 4.38 (q, 2H), 4.16 (t, 2H), 3.58 (s, 9H), 2.84-2.73 (m, 8H), 2.53 (quin, 2H), 1.74-1.60 (m, 8H), 1.48-1.27 (m, 27H), 0.92-0.85 (m, 12H) |
| No. 72 | 8.50 (d, 1H), 8.47 (s, 1H), 8.36 (s, 1H), 8.30 (s, 1H), 8.13 (d, 1H), 7.71 (d, 1H), 7.66-7.64 (m, 2H), 7.51-7.34 (m, 5H), 7.27-7.19 (m, 4H), 7.03 (s, 1H), 7.00 (s, 1H), 6.96 (s, 1H), 5.07 (s, 2H), 4.38 (q, 2H), 3.53 (s, 9H), 2.84-2.73 (m, 8H), 1.76-1.59 (m, 8H), 1.47-1.26 (m, 27H), 0.94-0.85 (m, 12H) |

Support materials according to the invention were prepared by the procedure described below using the compounds synthesized as described above.

Example 1

Support Material (Working Electrode) Produced with Compound No. 1

First prepared was the conductive substrate 11 made of a 2.0 cm long, 1.5 cm wide, 1.1 mm thick conductive glass substrate (F—SnO₂). Subsequently, 70 μm thick masking tapes were bonded to the conductive substrate 11 so as to surround a 0.5 cm long, 0.5 cm wide square area, and 3 cm³ of a metal oxide slurry was applied in uniform thickness to the square area and then dried. The metal oxide slurry used was a suspension of 10% by weight of titanium oxide powder (TiO₂, Ti-Nanoxide D manufactured by Solaronix SA.) in water. Subsequently, the masking tapes were peeled off from the conductive substrate 11, and the substrate was fired at 450° C. in an electric furnace, so that the metal oxide semiconductor layer 12 with a thickness of about 5 μm was formed. Subsequently, compound No. 1 was dissolved at a concentration of $3 \times 10^{-4}$ mol/dm³ in toluene to form a dye solution. The conductive substrate 11 with the metal oxide semiconductor layer 12 formed thereon was immersed in the dye solution, so that the dye 13-carrying working electrode 10 was formed.

The formed working electrode 10 was immersed in a remover (acetonitrile:water=99:1) under the conditions of 25° C. and 24 hours. Table 3 shows the ratio of the amount of the supported dye (the absorbance (Abs.) of the dye at λmax) after the immersion in the remover based on the amount of the supported dye before the immersion in the remover, as a measure of the resistance to removal, where the amount of the supported dye before the immersion in the remover is normalized as 100. It can be concluded that the closer to 100 the ratio of the amount of the supported dye after the removal is, the higher the resistance to removal.

Examples 2 to 29 and Comparative Examples 1 to 4

The working electrode 10 carrying each compound was prepared using the same process as in Example 1, except that compound No. 1 was replaced by the compound shown in Table 3, and the resistance of the dye to removal was determined as in Example 1. The results are shown in Table 3.

TABLE 3

| | Compound synthesized in Each of Synthesis Examples 1 to 29 | Resistance to Removal |
|---|---|---|
| Example 1 | No. 1 | 88 |
| Example 2 | No. 2 | 91 |

TABLE 3-continued

| | Compound synthesized in Each of Synthesis Examples 1 to 29 | Resistance to Removal |
|---|---|---|
| Example 3 | No. 3 | 89 |
| Example 4 | No. 4 | 89 |
| Example 5 | No. 5 | 93 |
| Example 6 | No. 6 | 88 |
| Example 7 | No. 7 | 95 |
| Example 8 | No. 8 | 99 |
| Example 9 | No. 9 | 85 |
| Example 10 | No. 10 | 93 |
| Example 11 | No. 11 | 82 |
| Example 12 | No. 12 | 93 |
| Example 13 | No. 13 | 94 |
| Example 14 | No. 14 | 86 |
| Example 15 | No. 15 | 97 |
| Example 16 | No. 16 | 99 |
| Example 17 | No. 17 | 91 |
| Example 18 | No. 18 | 88 |
| Example 19 | No. 19 | 92 |
| Example 20 | No. 20 | 87 |
| Example 21 | No. 21 | 98 |
| Example 22 | No. 22 | 86 |
| Example 23 | No. 23 | 88 |
| Example 24 | No. 24 | 84 |
| Example 25 | No. 61 | 98 |
| Example 26 | No. 62 | 99 |
| Example 27 | No. 70 | 99 |
| Example 28 | No. 71 | 91 |
| Example 29 | No. 72 | 96 |
| Comparative Example 1 | Comparative Compound 1 | 77 |
| Comparative Example 2 | Comparative Compound 2 | 71 |
| Comparative Example 3 | Comparative Compound 3 | 69 |
| Comparative Example 4 | Comparative Compound 4 | 67 |

[Chemical Formula 18]

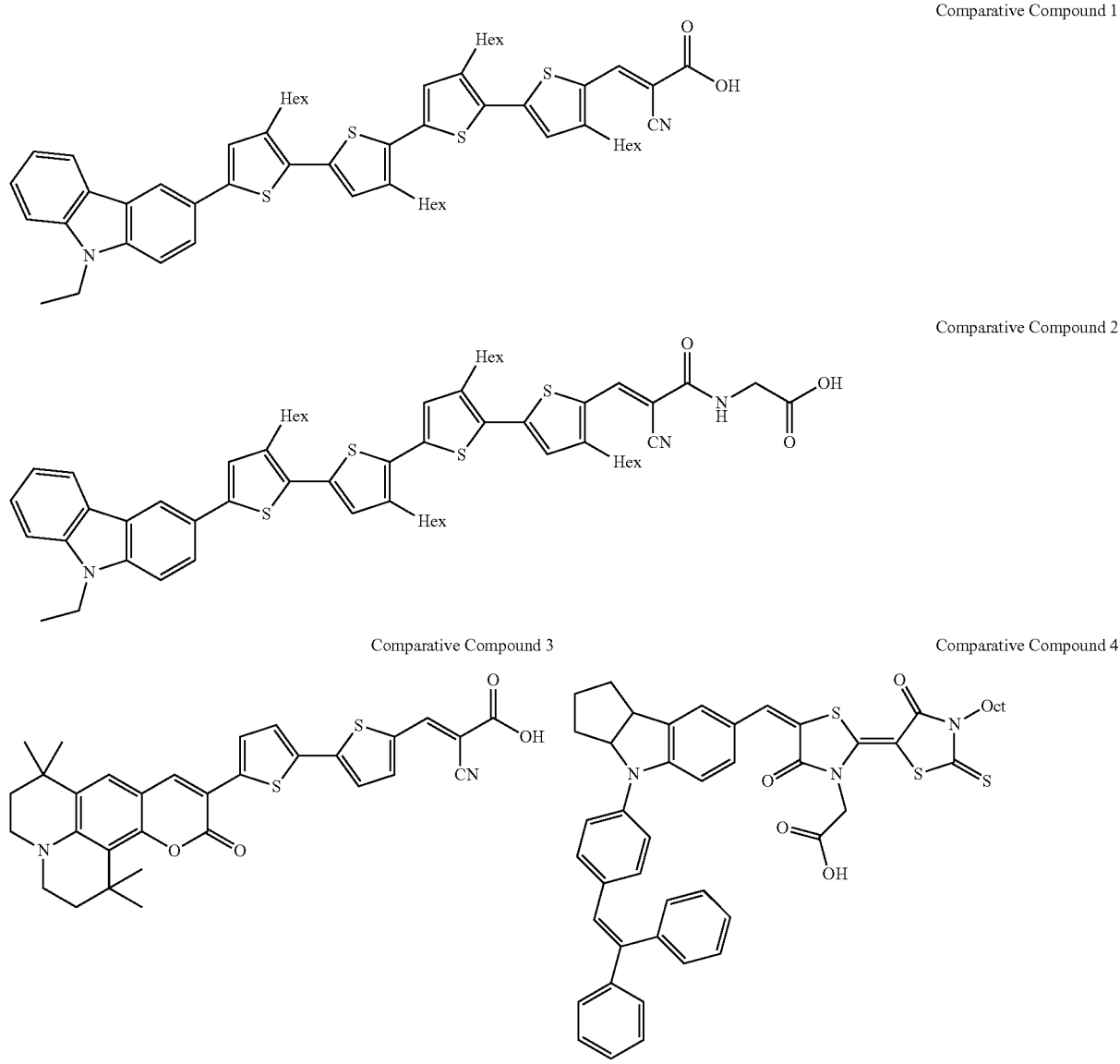

The results of the resistance to removal in Table 3 show that the compound of the invention represented by formula (1) has high adsorption durability.

The following are examples of the photoelectric conversion device of the invention and <Conversion Efficiency Evaluation of Photoelectric Conversion Device>.

Examples 30 to 42 and Comparative Examples 5 to 8

A counter electrode 20 was produced by coating an ITO electrode (produced by Nishinoda Electronics Co. Ltd.) as a conductive substrate with graphite particles (conductive layer 22). As shown in FIG. 1, a working electrode 10 produced using the support material (working electrode) prepared in each of Examples 1 to 11, 27 to 29, and Comparative Examples 1 to 4 was opposed via a spacer (63 μm) to the counter electrode 20 produced as above, then an electrolyte-containing layer 30 was disposed therebetween and fixed then with a clip, and then the electrolyte-containing layer 30 was impregnated with an electrolyte [a mixture prepared by mixing 4-tert-butylpyridine (0.5 mol/dm$^3$), lithium iodide (0.5 mol/dm$^3$), and iodine (0.05 mol/dm$^3$) with acetonitrile into prescribed concentrations, respectively]. Thus, a photoelectric conversion device was produced. The top of the cell was covered with a mask with an opening sized 1 cm$^2$, and then the conversion efficiency was measured with a solar simulator AM-1.5 (1000 W/m$^2$). The results are shown in Table 4.

TABLE 4

| | Compound in Working Electrode | | Conversion Efficiency |
|---|---|---|---|
| Example 30 | Example 1 | No. 1 | 2.4 |
| Example 31 | Example 2 | No. 2 | 2.2 |
| Example 32 | Example 3 | No. 3 | 2.1 |
| Example 33 | Example 4 | No. 4 | 3.2 |
| Example 34 | Example 5 | No. 5 | 3.0 |
| Example 35 | Example 6 | No. 6 | 2.7 |
| Example 36 | Example 7 | No. 7 | 2.4 |
| Example 37 | Example 8 | No. 8 | 2.5 |
| Example 38 | Example 10 | No. 10 | 2.2 |
| Example 39 | Example 11 | No. 11 | 2.4 |
| Example 40 | Example 27 | No. 70 | 2.1 |
| Example 41 | Example 28 | No. 71 | 2.3 |
| Example 42 | Example 29 | No. 72 | 2.1 |
| Comparative Example 5 | Comparative Example 1 | Comparative Compound 1 | 1.9 |
| Comparative Example 6 | Comparative Example 2 | Comparative Compound 2 | 1.6 |
| Comparative Example 7 | Comparative Example 3 | Comparative Compound 3 | 2.0 |
| Comparative Example 8 | Comparative Example 4 | Comparative Compound 4 | 1.6 |

The following are examples of the photoelectric conversion device of the invention and <Conversion Efficiency Evaluation of Photoelectric Conversion Device> wherein the material of the metal oxide semiconductor was changed.

Examples 43 to 45 and Comparative Example 9

By the same operations as in Example 1 except that compound No. 1 was replaced by the compounds shown in Table 4A and the titanium oxide powder was replaced by zinc oxide (ZnO, produced by SOLAR CO., Ltd.), working electrodes 10 carrying the respective compounds were produced. Using the resulting working electrodes 10, conversion efficiency was measured by the same operations as in Example 30. The results are shown in Table 4A.

TABLE 4A

| | Compound | Conversion Efficiency |
|---|---|---|
| Example 43 | No. 4 | 1.3 |
| Example 44 | No. 7 | 1.3 |
| Example 45 | No. 8 | 1.4 |
| Comparative Example 9 | Comparative Compound 1 | 0.8 |

The measurements given above of the conversion efficiency of the photoelectric conversion devices clearly show that the support material and the photoelectric conversion device of the invention exhibit high conversion efficiency as is notable in comparison between similar compounds (comparison of Examples 30 to 37 and 40 to 42 with Comparative Examples 5 and 6, comparison of Examples 38 and 39 with Comparative Example 7, and comparison of Examples 43 to 45 with Comparative Example 9).

<Evaluation of Photoresistance>

Evaluation of photoresistance was carried out for the support materials (working electrodes) prepared in Examples 4 and 7 and Comparative Examples 1 and 2. In the evaluation, each of the working electrode was irradiated with light at 55000 Lux for 4 hours, and then the change in λmax of the UV absorption spectrum was calculated where the value before the irradiation was normalized as 100. Specifically, Abs. after the irradiation and Abs. before the irradiation at λmax were measured, and then "(Abs. after irradiation/Abs. after irradiation)×100" was calculated and used as the value of photoresistance. The results are shown in Table 5.

TABLE 5

| | Compound | Photoresistance |
|---|---|---|
| Example 4 | No. 4 | 79 |
| Example 7 | No. 7 | 93 |
| Comparative Example 1 | Comparative Compound 1 | 64 |
| Comparative Example 2 | Comparative Compound 2 | 69 |

According to the results shown above, the support material of the invention is useful because it excels in resistance to removal and light resistance and apparently exhibits high conversion efficiency when used for a photoelectric conversion device.

The invention claimed is:

1. A novel compound having a general formula (1):

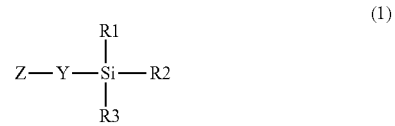

wherein

Z is a conjugated group,

Y is selected from the group consisting of:

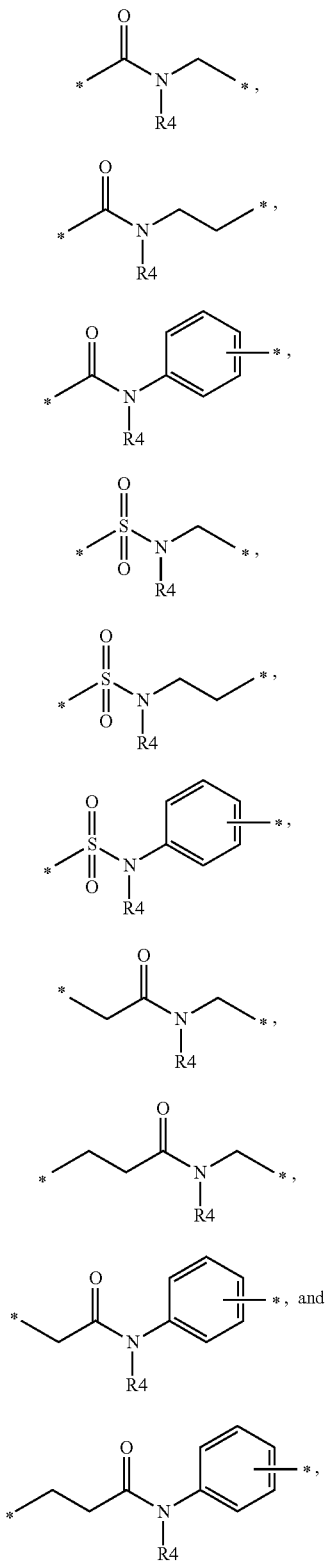

wherein

R4 is a hydrogen atom or an optionally substituted hydrocarbon group having 1 to 20 carbon atoms, R4 and Z may be linked together to form a ring, any hydrogen atom in the formulae may be substituted with a fluorine atom, a chlorine atom, a bromine atom, an iodine atom, a cyano group, a nitro group, an —OR7 group, an —SR7 group, or an —NR7R8 group, R7 and R8 each is a hydrogen atom or an optionally substituted hydrocarbon group, and any benzene ring in the formulae may be substituted with an aliphatic hydrocarbon group having 1 to 4 carbon atoms, and R1, R2, and R3 each is an optionally substituted hydrocarbon group or an optionally substituted hydrocarbonoxy group, at least one of R1, R2, and R3 is an optionally substituted hydrocarbonoxy group.

2. The novel compound according to claim 1, wherein R1, R2, and R3 in formula (1) are each a linear or branched aliphatic hydrocarbonoxy group.

3. The novel compound according to claim 1, wherein Z in formula (1) has a partial structural formula (2),

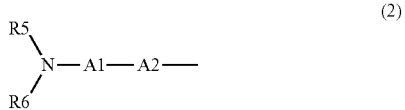

wherein

A1 is an optionally substituted aromatic hydrocarbon ring group or an optionally substituted aromatic heterocyclic group, A2 is a direct bond or a group comprising a chain of one to seven pieces of one or more groups selected from the group consisting of:

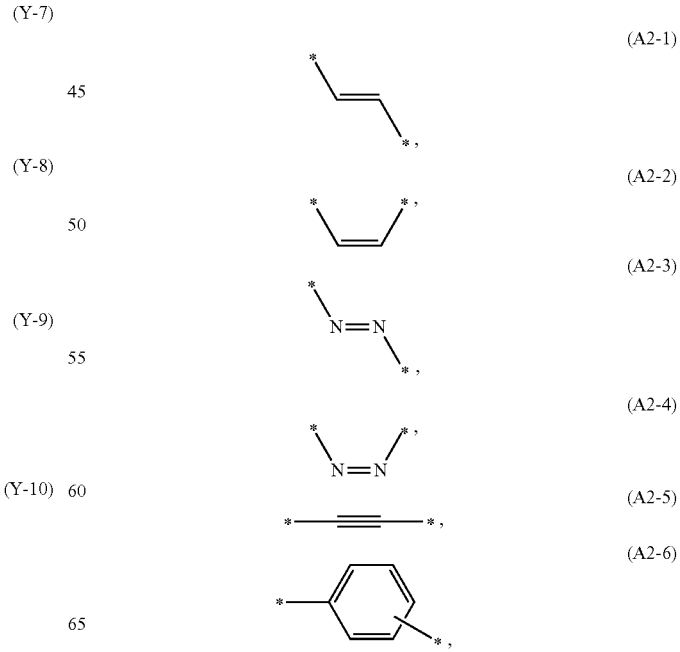

-continued

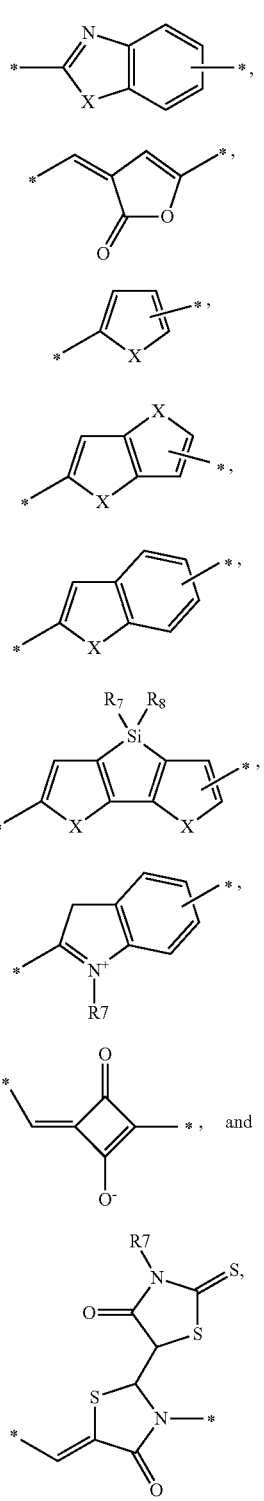

wherein
X is S, O, or NR,
R is a hydrogen atom or an optionally substituted hydrocarbon group, and
any hydrogen atoms in the formulae may be substituted with a fluorine atom, a chlorine atom, an iodine atom, a cyano group, a nitro group, an —OR7 group, an —SR7 group, an —NR7R8 group, or an optionally substituted aliphatic hydrocarbon group, wherein R7 and R8 each is a hydrogen atom or an optionally substituted hydrocarbon group, R5 and R6 each is an optionally substituted hydrocarbon group, R5 and R6 may be linked together to form a ring, and R5 and R6 may be each independently linked with A1 to form a ring.

4. The novel compound according to claim 1, wherein partial structure (3),

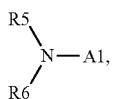  (3)

in partial structural formula (2) is selected from the group consisting of:

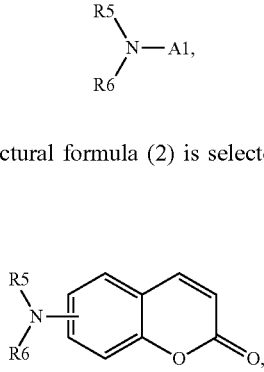  (3-1)

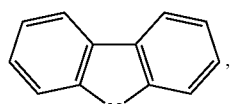  (3-2)

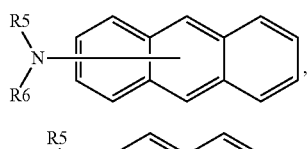  (3-3)

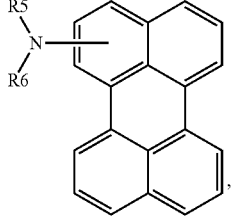  (3-4)

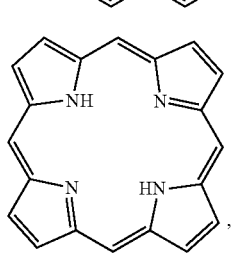  (3-5)

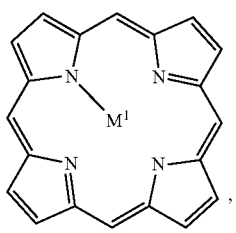  (3-6)

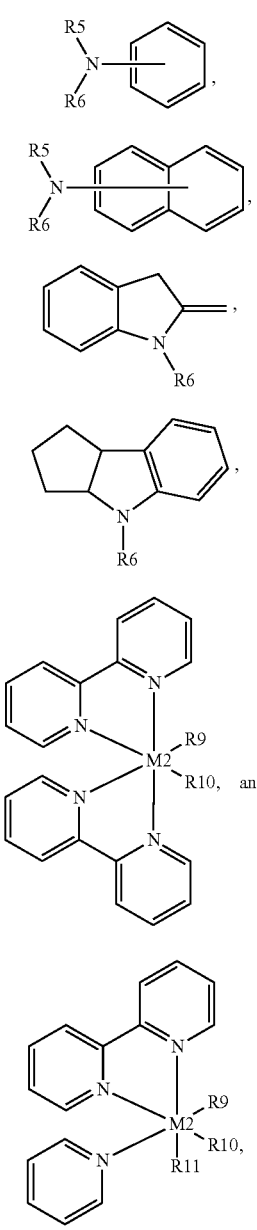

wherein
  R5 and R6 are the same as those of partial structural formula (2),
  R9, R10, and R11 each is a known ligand that coordinates to M2,
  M1 and M2 each is a metal element, and
  any hydrogen atoms in the formulae may be substituted with a fluorine atom, a chlorine atom, an iodine atom, a cyano group, a nitro group, an —OR7 group, an —SR7 group, or an optionally substituted aliphatic hydrocarbon group, wherein R7 and R8 each is a hydrogen atom or an optionally substituted hydrocarbon group.

5. A support material comprising a support and a compound having a formula (1) supported on the support,

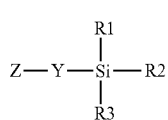

wherein
  Y is an optionally substituted hydrocarbon group having 1 to 20 carbon atoms and having —CO—NR4- or —SO$_2$—NR4- in the group,
  Z is a conjugated group,
  R1, R2, and R3 each is an optionally substituted hydrocarbon group or an optionally substituted hydrocarbonoxy group,
  at least one of R1, R2, and R3 is an optionally substituted hydrocarbonoxy group,
  R4 is a hydrogen atom or an optionally substituted hydrocarbon group having 1 to 20 carbon atoms, and
  R4 and Z may be linked together to form a ring.

6. The support material according to claim 5, wherein R1, R2, and R3 in formula (1) each is a linear or branched aliphatic hydrocarbonoxy group.

7. A photoelectric conversion device comprising an electrode having the support material according to claim 5.

8. The novel compound according to claim 2, wherein Z in formula (1) having a partial structural formula (2),

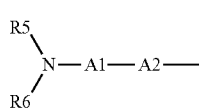

wherein
  A1 is an optionally substituted aromatic hydrocarbon ring group or an optionally substituted aromatic heterocyclic group,
  A2 is a direct bond or a group comprising a chain of one to seven pieces of one or more groups selected from the group consisting of:

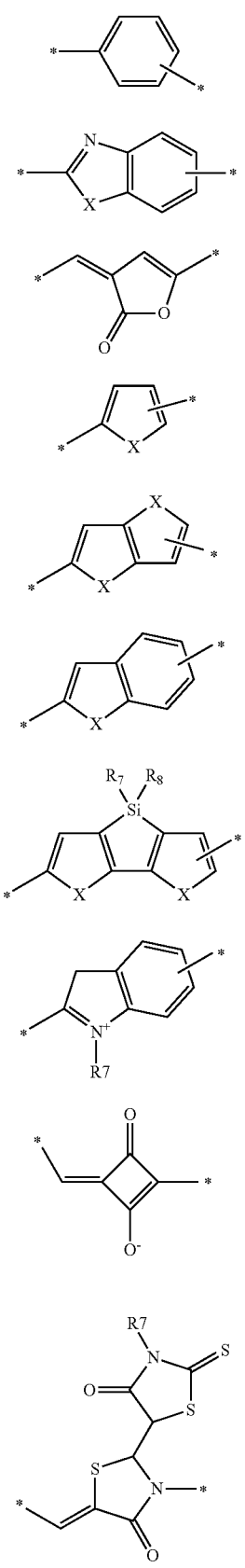

wherein
X is S, O, or NR,
R is a hydrogen atom or an optionally substituted hydrocarbon group, and
any hydrogen atoms in the formulae may be substituted with a fluorine atom, a chlorine atom, an iodine atom, a cyano group, a nitro group, an —OR7 group, an —SR7 group, an —NR7R8 group, or an optionally substituted aliphatic hydrocarbon group, wherein R7 and R8 each is a hydrogen atom or an optionally substituted hydrocarbon group,
R5 and R6 each is an optionally substituted hydrocarbon group,
R5 and R6 may be linked together to form a ring, and
R5 and R6 may be each independently linked with A1 to form a ring.

9. The novel compound according to claim 2, wherein partial structure (3) in partial structural formula (2) is selected from the group consisting of:

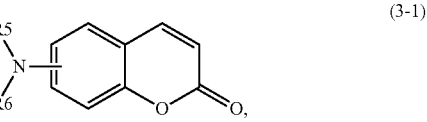

(3-1)

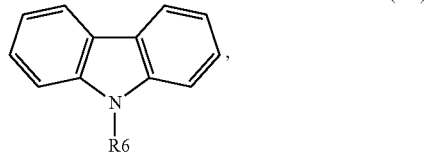

(3-2)

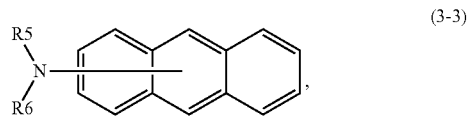

(3-3)

(3-4)

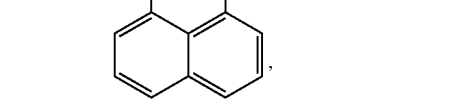

(3-5)

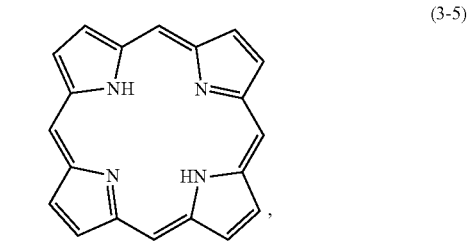

(3-6)

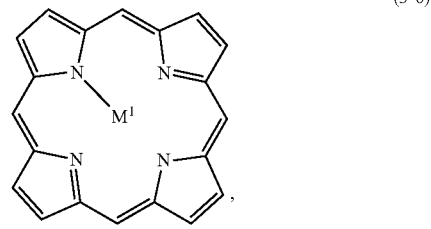

-continued

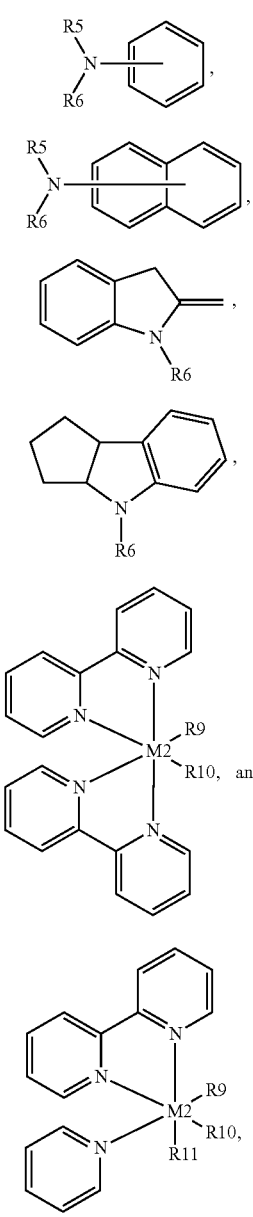

(3-7)

(3-8)

(3-9)

(3-10)

(3-11)

(3-12)

wherein

R5 and R6 are the same as those of partial structural formula (2),

R9, R10, and R11 each is a known ligand that coordinates to M2,

M1 and M2 each is a metal element, and any hydrogen atoms in the formulae may be substituted with a fluorine atom, a chlorine atom, an iodine atom, a cyano group, a nitro group, an —OR7 group, an —SR7 group, or an optionally substituted aliphatic hydrocarbon group, wherein R7 and R8 each is a hydrogen atom or an optionally substituted hydrocarbon group.

10. The novel compound according to claim 3, wherein partial structure (3) in partial structural formula (2) is selected from the group consisting of:

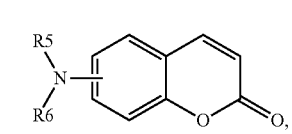
(3-1)

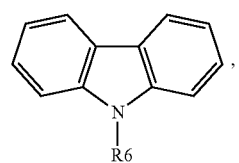
(3-2)

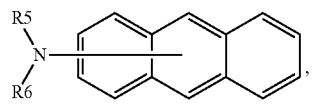
(3-3)

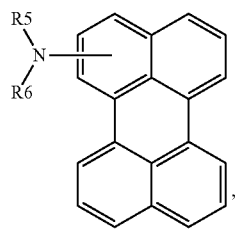
(3-4)

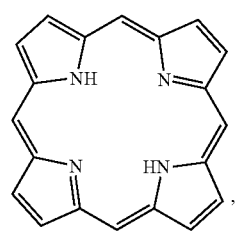
(3-5)

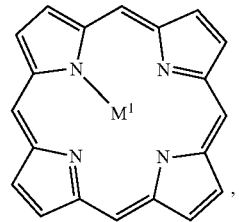
(3-6)

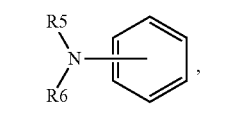
(3-7)

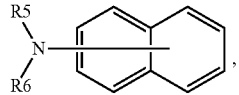
(3-8)

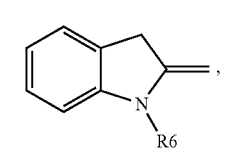
(3-9)

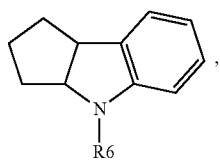
(3-10)

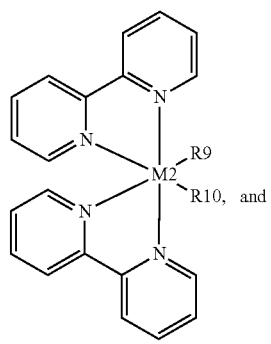
(3-11)

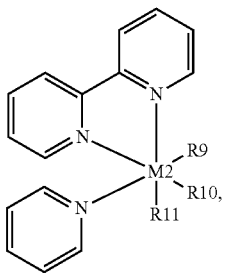
(3-12)

R5 and R6 are the same as those of partial structural formula (2),

R9, R10, and R11 each is a known ligand that coordinates to M2,

M1 and M2 each is a metal element, and any hydrogen atoms in the formulae may be substituted with a fluorine atom, a chlorine atom, an iodine atom, a cyano group, a nitro group, an —OR7 group, an —SR7 group, or an optionally substituted aliphatic hydrocarbon group, wherein R7 and R8 each is a hydrogen atom or an optionally substituted hydrocarbon group.

11. A photoelectric conversion device comprising an electrode having the support material according to claim 6.

* * * * *